United States Patent
Zhu et al.

(10) Patent No.: US 11,452,771 B2
(45) Date of Patent: Sep. 27, 2022

(54) SCAFFOLDED HIV-1 ENV GP140 TRIMER IMMUNOGEN

(71) Applicant: The Scripps Research Institute, La Jolla, CA (US)

(72) Inventors: Jiang Zhu, San Diego, CA (US); Linling He, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 13 days.

(21) Appl. No.: 17/021,821

(22) Filed: Sep. 15, 2020

(65) Prior Publication Data

US 2021/0030884 A1 Feb. 4, 2021

Related U.S. Application Data

(62) Division of application No. 16/177,165, filed on Oct. 31, 2018, now Pat. No. 10,780,178.

(60) Provisional application No. 62/580,038, filed on Nov. 1, 2017.

(51) Int. Cl.
| | |
|---|---|
| *A61K 39/12* | (2006.01) |
| *A61K 47/64* | (2017.01) |
| *A61P 31/18* | (2006.01) |
| *A61K 39/21* | (2006.01) |
| *A61K 9/51* | (2006.01) |
| *C07K 14/16* | (2006.01) |
| *A61K 38/16* | (2006.01) |
| *C07K 14/005* | (2006.01) |
| *A61K 47/69* | (2017.01) |
| *A61K 39/00* | (2006.01) |

(52) U.S. Cl.
CPC ............... *A61K 39/12* (2013.01); *A61K 9/51* (2013.01); *A61K 38/162* (2013.01); *A61K 39/21* (2013.01); *A61K 47/646* (2017.08); *A61P 31/18* (2018.01); *C07K 14/005* (2013.01); *C07K 14/162* (2013.01); *A61K 47/69* (2017.08); *A61K 2039/55555* (2013.01); *A61K 2039/55561* (2013.01); *A61K 2039/57* (2013.01); *A61K 2039/575* (2013.01); *C12N 2740/16023* (2013.01); *C12N 2740/16122* (2013.01); *C12N 2740/16134* (2013.01)

(58) Field of Classification Search
CPC ........ A61K 39/21; A61K 9/51; C07K 14/162; C12N 2740/16122; C12N 2740/16134
See application file for complete search history.

(56) References Cited

U.S. PATENT DOCUMENTS

| 5,736,142 A | 4/1998 | Sette et al. |
| 8,546,337 B2 | 10/2013 | Burkhard |
| 9,932,370 B2 | 4/2018 | Barouch et al. |

| 2006/0228357 A1 | 10/2006 | Chang et al. |
| 2014/0212458 A1 | 7/2014 | Caulfield et al. |
| 2017/0233441 A1 | 8/2017 | Kwong et al. |

FOREIGN PATENT DOCUMENTS

| WO | 2016/037154 A1 | 3/2016 |
| WO | 2016/138525 A1 | 9/2016 |
| WO | 2016/205704 A2 | 12/2016 |
| WO | 2017/152146 A2 | 9/2017 |

OTHER PUBLICATIONS

He, L., et al., Jun. 2016, Presenting native-like trimeric HIV-1 antigens with self-assembling nanoparticles, Nat. Comm. 7:12041, pp. 1-15.*
Hsia, Y., et al., Jul. 2016, Design of a hyperstable 60-subunit protein icosahedron, Nature 535:136-148.*
Yang, X., et al., Characterization of stable, soluble trimers containing complete ectodomains of human immunodeficiency virus type 1 envelope glycoproteins. J Virol. 74(12):5716-25 (2000).
Yang, X., et al., Modifications that stabilize human immunodeficiency virus envelope glycoprotein trimers in solution. J Virol. 74(10):4746-54 (2000).
Yang, X., et al., Highly stable trimers formed by human immunodeficiency virus type 1 envelope glycoproteins fused with the trimeric motif of T4 bacteriophage fibritin. J Virol. 76(9):4634-42 (2002).
Sanders, R.W., et al., Stabilization of the soluble, cleaved, trimeric form of the envelope glycoprotein complex of human immunodeficiency virus type 1. J Virol. 76(17):8875-89 (2002).
Sanders, R.W., et al., A next-generation cleaved, soluble HIV-1 Env trimer, BG505 SOSIP.664 gp140, expresses multiple epitopes for broadly neutralizing but not non-neutralizing antibodies. PLoS Pathog. 9(9):e1003618 (2013).
Sharma, S.K., et al., Cleavage-independent HIV-1 Env trimers engineered as soluble native spike mimetics for vaccine design. Cell Rep. 11(4):539-50 (2015).
Guenaga, J., et al., Structure-Guided Redesign Increases the Propensity of HIV Env To Generate Highly Stable Soluble Trimers. J Virol. 90(6):2806-17 (2015).

(Continued)

*Primary Examiner* — Jeffrey S Parkin
(74) *Attorney, Agent, or Firm* — Hugh Wang; Thomas Fitting

(57) ABSTRACT

The present invention provides novel scaffolded HIV-1 vaccine immunogens. Some of the scaffolded immunogens contain a soluble gp140 trimer linked to the N-terminus of the nanoparticle subunit and a T-helper epitope that is fused via a short peptide spacer to the C-terminus of the nanoparticle subunit. Some other immunogens of the invention contain a soluble gp140 trimer protein that is linked to a stable nanoparticle via a short peptide spacer that is a T-helper epitope. Some of the scaffolded immunogens contain a gp140 trimer immunogen presented on a nanoparticle platform formed with I3-01 protein, E2p, or variants of protein 1VLW. Also provided in the invention are nucleic acids that encode the various vaccine immunogens described herein, and expression vectors and host cells harboring the nucleic acids. The invention further provides methods of using the scaffolded HIV-1 vaccine immunogens for preventing or treating HIV infections.

21 Claims, 12 Drawing Sheets

Specification includes a Sequence Listing.

(56) References Cited

OTHER PUBLICATIONS

Georgiev, I.S., et al., Single-Chain Soluble BG505.SOSIP gp140 Trimers as Structural and Antigenic Mimics of Mature Closed HIV-1 Env. J Virol 89(10):5318-29 (2015).
Jardine, J., et al., Rational HIV immunogen design to target specific germline B cell receptors. Science. 340 (6133):711-6 (2013).
Sliepen, K., et al., Presenting native-like HIV-1 envelope trimers on ferritin nanoparticles improves their immunogenidty. Retrovirology. 12:82 (2015).
Kong, L. et al., Uncleaved prefusion-optimized gp140 trimers derived from analysis of HIV-1 envelope metastability. Nat Commun. 7:12040 (2016).
He, L., et al., Presenting native-like trimeric HIV-1 antigens with self-assembling nanoparticles. Nat Commun. 7:12041 (2016).
White, et al., Crit Rev Biochem Mol Biol. 2008 ; 43(3): 189-219.
Krarup, et al., Nature Communications 6:8143, 2015.
Bissati, et al., Vaccines 32:3243-3248, 2014.
Gallo, Robert C., The End or the Beginning of the Drive to an HIV-Preventive Vaccine—a View from over 20 Years, The Lancet, vol. 366, p. 1894-1898, 2005.
He, et al., HIV-1 vaccine design through minimizing envelope metastability, Science Advances, 4, 1-19, 2018.
Hu, et al., Murine Antibody Responses to Cleaved Soluble HIV-1 Envelope Trimers Are Highly Restricted in Specificity, Journal of Virology, 89:20, 2015.
Rios, Adan, Fundamental Challenges to the Development of a Preventive HIV Vaccine, 29:26-32, 2018.
West, et al., Structural Insights on the Role of Antibodies in HIV-1 and Therapy, Cell, 156:633-648, 2014.
Hsia, et al., Design of Hyperstable 60-subunit Protein Icosahdedron, Nature 535:136-150, 2016.

\* cited by examiner

HIV-1 NEUTRALIZATION BY GROUP-COMBINED MOUSE SERUM IgG (IC50, 1:X)

| | S1G3 | S1G4 | S1G5 | S1G6 | S1G7 |
|---|---|---|---|---|---|
| TIER-2 CLADE-A BG505.N332 | < 80 | < 80 | 91 | < 80 | < 80 |
| TIER-1 CLADE-B SF162 | 231 | 222 | 65 | 141 | 905 |
| MLV (CONTROL) | < 80 | < 80 | < 80 | < 80 | < 80 |
| | S2G1 | S1G8 | S1G9 | S1G10 | S2G5 |
| TIER-2 CLADE-A BG505.N332 | 248 | < 80 | < 80 | < 80 | 2427 |
| TIER-1 CLADE-B SF162 | 297 | 192 | 108 | < 80 | 376 |
| MLV (CONTROL) | < 80 | < 80 | < 80 | < 80 | < 80 |
| | S2G6 | S2G7 | S1G0 | | |
| TIER-2 CLADE-A BG505.N332 | 137 | < 80 | < 80 | | |
| TIER-1 CLADE-B SF162 | 396 | 229 | < 80 | | |
| MLV (CONTROL) | < 80 | < 80 | < 80 | | |

SEQUENCE LISTING

```
<160> NUMBER OF SEQ ID NOS: 20

<210> SEQ ID NO 1
<211> LENGTH: 13
<212> TYPE: PRT
<213> ORGANISM: Artificial Sequence
<220> FEATURE:
<223> OTHER INFORMATION: Synthetic sequence

<400> SEQUENCE: 1

Ala Lys Phe Val Ala Ala Trp Thr Leu Lys Ala Ala Ala
1               5                   10

<210> SEQ ID NO 2
<211> LENGTH: 15
<212> TYPE: PRT
<213> ORGANISM: Artificial sequence
<220> FEATURE:
<223> OTHER INFORMATION: Synthetic sequence

<400> SEQUENCE: 2

Gln Ser Ile Ala Leu Ser Ser Leu Met Val Ala Gln Ala Ile Pro
1               5                   10                  15

<210> SEQ ID NO 3
<211> LENGTH: 32
<212> TYPE: PRT
<213> ORGANISM: Artificial sequence
<220> FEATURE:
<223> OTHER INFORMATION: Synthetic sequence

<400> SEQUENCE: 3

Ile Leu Met Gln Tyr Ile Lys Ala Asn Ser Lys Phe Ile Gly Ile Pro
1               5                   10                  15

Met Gly Leu Pro Gln Ser Ile Ala Leu Ser Ser Leu Met Val Ala Gln
                20                  25                  30
```

<210> SEQ ID NO 4
<211> LENGTH: 5
<212> TYPE: PRT
<213> ORGANISM: Artificial sequence
<220> FEATURE:
<223> OTHER INFORMATION: Synthetic sequence

<400> SEQUENCE: 4

Gly Gly Gly Gly Ser
1               5

<210> SEQ ID NO 5
<211> LENGTH: 205
<212> TYPE: PRT
<213> ORGANISM: Thermotoga maritima

<400> SEQUENCE: 5

Met Lys Met Glu Glu Leu Phe Lys Lys His Lys Ile Val Ala Val Leu
1               5                   10                  15

Arg Ala Asn Ser Val Glu Glu Ala Lys Glu Lys Ala Leu Ala Val Phe
                20                  25                  30

Glu Gly Gly Val His Leu Ile Glu Ile Thr Phe Thr Val Pro Asp Ala
            35                  40                  45

Asp Thr Val Ile Lys Glu Leu Ser Phe Leu Lys Glu Lys Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Thr Ile Leu
            115                 120                 125

Lys Leu Phe Pro Gly Glu Val Val Gly Pro Gln Phe Val Lys Ala Met
        130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Asp Glu Val Arg Glu Lys
            180                 185                 190

Ala Lys Ala Phe Val Glu Lys Ile Arg Gly Cys Thr Glu
        195                 200                 205

<210> SEQ ID NO 6
<211> LENGTH: 205
<212> TYPE: PRT
<213> ORGANISM: Artificial sequence
<220> FEATURE:
<223> OTHER INFORMATION: Synthetic sequence

<400> SEQUENCE: 6

Met Lys Met Glu Glu Leu Phe Lys Lys His Lys Ile Val Ala Val Leu
1               5                   10                  15

Arg Ala Asn Ser Val Glu Glu Ala Lys Lys Lys Ala Leu Ala Val Phe
                20                  25                  30

Leu Gly Gly Val His Leu Ile Glu Ile Thr Phe Thr Val Pro Asp Ala
            35                  40                  45

Asp Thr Val Ile Lys Glu Leu Ser Phe Leu Lys Glu Met Gly Ala Ile
            50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Ile
            85                  90                  95

Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Thr Ile Leu
            115                 120                 125

Lys Leu Phe Pro Gly Glu Val Val Gly Pro Gln Phe Val Lys Ala Met
130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Cys Glu Val Ala Cys Lys
            180                 185                 190

Ala Lys Ala Phe Val Glu Lys Ile Arg Gly Cys Thr Glu
            195                 200                 205

<210> SEQ ID NO 7
<211> LENGTH: 205
<212> TYPE: PRT
<213> ORGANISM: Artificial sequence
<220> FEATURE:
<223> OTHER INFORMATION: Synthetic sequence

<400> SEQUENCE: 7

Met Lys Met Glu Glu Leu Phe Lys Lys His Lys Ile Val Ala Val Leu
1               5                   10                  15

Arg Ala Asn Ser Val Glu Glu Ala Lys Trp Lys Ala Leu Ala Val Phe
            20                  25                  30

Ile Gly Gly Val His Leu Ile Glu Ile Thr Phe Thr Val Pro Asp Ala
            35                  40                  45

Asp Thr Val Ile Lys Glu Leu Ser Phe Leu Lys Glu Leu Gly Ala Ile
            50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Ile
            85                  90                  95

Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Thr Ile Leu
            115                 120                 125

Lys Leu Phe Pro Gly Glu Val Val Gly Pro Gln Phe Val Lys Ala Met
130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Pro Ala Glu Val Val Glu Lys
            180                 185                 190

Ala Lys Ala Phe Val Glu Lys Ile Arg Gly Cys Thr Glu
            195                 200                 205

```
<210> SEQ ID NO 8
<211> LENGTH: 205
<212> TYPE: PRT
<213> ORGANISM: Artificial sequence
<220> FEATURE:
<223> OTHER INFORMATION: Synthetic sequence

<400> SEQUENCE: 8

Met Lys Met Glu Glu Leu Phe Lys Lys His Lys Ile Val Ala Val Leu
1               5                   10                  15

Arg Ala Asn Ser Val Glu Glu Ala Lys Met Lys Ala Leu His Val Phe
            20                  25                  30

Ser Gly Gly Val His Leu Ile Glu Ile Thr Phe Thr Val Pro Asp Ala
        35                  40                  45

Asp Thr Val Ile Lys Glu Leu Ser Phe Leu Lys Glu Gln Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Trp Asp Glu Val Ser Arg Lys
            180                 185                 190

Ala Lys Ala Phe Val Glu Lys Ile Arg Gly Cys Thr Glu
        195                 200                 205

<210> SEQ ID NO 9
<211> LENGTH: 205
<212> TYPE: PRT
<213> ORGANISM: Artificial sequence
<220> FEATURE:
<223> OTHER INFORMATION: Synthetic sequence

<400> SEQUENCE: 9

Met Lys Met Glu Glu Leu Phe Lys Lys His Lys Ile Val Ala Val Leu
1               5                   10                  15

Arg Ala Asn Ser Val Glu Glu Ala Lys Trp Lys Ala Leu His Val Phe
            20                  25                  30

Thr Gly Gly Val His Leu Ile Glu Ile Thr Phe Thr Val Pro Asp Ala
        35                  40                  45

Asp Thr Val Ile Lys Glu Leu Ser Phe Leu Lys Glu Gln Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
```

```
                  100                 105                 110

Thr Pro Thr Glu Leu Val Lys Ala Met Lys Leu Gly His Thr Ile Leu
            115                 120                 125

Lys Leu Phe Pro Gly Glu Val Gly Pro Gln Phe Val Lys Ala Met
130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Trp His Glu Val Ala Ala Lys
            180                 185                 190

Ala Lys Ala Phe Val Glu Lys Ile Arg Gly Cys Thr Glu
            195                 200                 205

<210> SEQ ID NO 10
<211> LENGTH: 205
<212> TYPE: PRT
<213> ORGANISM: Artificial sequence
<220> FEATURE:
<223> OTHER INFORMATION: Synthetic sequence

<400> SEQUENCE: 10

Met Lys Met Glu Glu Leu Phe Lys Lys His Lys Ile Val Ala Val Leu
1               5                   10                  15

Arg Ala Asn Ser Val Glu Glu Ala Lys Met Lys Ala Leu His Val Phe
            20                  25                  30

Thr Gly Gly Val His Leu Ile Glu Ile Thr Phe Thr Val Pro Asp Ala
        35                  40                  45

Asp Thr Val Ile Lys Glu Leu Ser Phe Leu Lys Glu Trp Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Trp Asp Glu Val Ala Ala Lys
            180                 185                 190

Ala Lys Ala Phe Val Glu Lys Ile Arg Gly Cys Thr Glu
        195                 200                 205

<210> SEQ ID NO 11
<211> LENGTH: 205
<212> TYPE: PRT
<213> ORGANISM: Artificial sequence
<220> FEATURE:
<223> OTHER INFORMATION: Synthetic sequence

<400> SEQUENCE: 11
```

Met Lys Met Glu Glu Leu Phe Lys Lys His Lys Ile Val Ala Val Leu
1               5                   10                  15

Arg Ala Asn Ser Val Glu Glu Ala Lys Lys Lys Ala Leu Ala Val Phe
                20                  25                  30

Leu Ala Gly Val His Leu Ile Glu Ile Thr Phe Thr Val Pro Asp Ala
            35                  40                  45

Asp Thr Val Ile Lys Glu Leu Ser Phe Leu Lys Glu Met Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Ile
                85                  90                  95

Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Thr Ile Leu
            115                 120                 125

Lys Leu Phe Pro Gly Glu Val Val Gly Pro Gln Phe Val Lys Ala Met
        130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Val Val Glu Val Ala Ala Lys
            180                 185                 190

Ala Ala Ala Phe Val Gly Lys Ile Arg Gly Cys Thr Glu
        195                 200                 205

<210> SEQ ID NO 12
<211> LENGTH: 205
<212> TYPE: PRT
<213> ORGANISM: Artificial sequence
<220> FEATURE:
<223> OTHER INFORMATION: Synthetic sequence

<400> SEQUENCE: 12

Met Lys Met Glu Glu Leu Phe Lys Lys His Lys Ile Val Ala Val Leu
1               5                   10                  15

Arg Ala Asn Ser Val Glu Glu Ala Lys Lys Lys Ala Leu Ala Val Phe
                20                  25                  30

Leu Gly Gly Val His Leu Ile Glu Ile Thr Phe Thr Val Pro Asp Ala
            35                  40                  45

Asp Thr Val Ile Lys Glu Leu Ser Phe Leu Lys Glu Met Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Ile
                85                  90                  95

Ser Gln Phe Cys Lys Glu Lys Gly Val Phe Tyr Met Pro Gly Val Met
                100                 105                 110

Thr Pro Thr Glu Leu Val Lys Ala Met Lys Leu Gly His Thr Ile Leu
            115                 120                 125

Lys Leu Phe Pro Gly Glu Val Val Gly Pro Gln Phe Val Lys Ala Met
        130                 135                 140

Lys Gly Pro Phe Pro Asn Val Lys Phe Val Pro Thr Gly Gly Val Asn
145                 150                 155                 160

```
Leu Asp Asn Val Cys Glu Trp Phe Lys Ala Gly Val Leu Ala Val Gly
            165                 170                 175

Val Gly Ser Ala Leu Val Lys Gly Thr Ile Val Glu Val Ala Ala Lys
        180                 185                 190

Ala Ala Ala Phe Val Glu Lys Ile Arg Gly Cys Thr Glu
        195                 200                 205

<210> SEQ ID NO 13
<211> LENGTH: 205
<212> TYPE: PRT
<213> ORGANISM: Artificial sequence
<220> FEATURE:
<223> OTHER INFORMATION: Synthetic sequence

<400> SEQUENCE: 13

Met Lys Met Glu Glu Leu Phe Lys Lys His Lys Ile Val Ala Val Leu
1               5                   10                  15

Arg Ala Asn Ser Val Glu Glu Ala Lys Lys Lys Ala Leu Ala Val Phe
            20                  25                  30

Leu Gly Gly Val His Leu Ile Glu Ile Thr Phe Thr Val Pro Asp Ala
        35                  40                  45

Asp Thr Val Ile Lys Glu Leu Ser Phe Leu Lys Glu Met Gly Ala Ile
50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
            85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
            165                 170                 175

Val Gly Ser Ala Leu Val Lys Gly Thr Trp Val Glu Val Ala Ala Lys
        180                 185                 190

Ala Ala Ala Phe Val Glu Lys Ile Arg Gly Cys Thr Glu
        195                 200                 205

<210> SEQ ID NO 14
<211> LENGTH: 205
<212> TYPE: PRT
<213> ORGANISM: Artificial sequence
<220> FEATURE:
<223> OTHER INFORMATION: Synthetic sequence

<400> SEQUENCE: 14

Met Lys Met Glu Glu Leu Phe Lys Lys His Lys Ile Val Ala Val Leu
1               5                   10                  15

Arg Ala Asn Ser Val Glu Glu Ala Lys Met Lys Ala Leu Gln Val Phe
            20                  25                  30

Val Gly Gly Val His Leu Ile Glu Ile Thr Phe Thr Val Pro Asp Ala
        35                  40                  45

Asp Thr Val Ile Lys Glu Leu Ser Phe Leu Lys Glu Ala Gly Ala Ile
50                  55                  60
```

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Ile
            85                  90                  95

Ser Gln Phe Cys Lys Glu Lys Val Phe Tyr Met Pro Gly Val Met
            100                 105                 110

Thr Pro Thr Glu Leu Val Lys Ala Met Lys Leu Gly His Thr Ile Leu
            115                 120                 125

Lys Leu Phe Pro Gly Glu Val Gly Pro Gln Phe Val Lys Ala Met
        130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Leu Ala Glu Val Ala Ala Lys
            180                 185                 190

Ala Glu Ala Phe Val Glu Lys Ile Arg Gly Cys Thr Glu
        195                 200                 205

<210> SEQ ID NO 15
<211> LENGTH: 205
<212> TYPE: PRT
<213> ORGANISM: Artificial sequence
<220> FEATURE:
<223> OTHER INFORMATION: Synthetic sequence

<400> SEQUENCE: 15

Met Lys Met Glu Glu Leu Phe Lys Lys His Lys Ile Val Ala Val Leu
1               5                   10                  15

Arg Ala Asn Ser Val Glu Glu Ala Lys Trp Lys Ala Leu His Val Phe
            20                  25                  30

Val Gly Gly Val His Leu Ile Glu Ile Thr Phe Thr Val Pro Asp Ala
        35                  40                  45

Asp Thr Val Ile Lys Glu Leu Ser Phe Leu Lys Glu Ala Gly Ala Ile
    50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Ile
            85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
            115                 120                 125

Lys Leu Phe Pro Gly Glu Val Val Gly Pro Gln Phe Val Lys Ala Met
        130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Trp Ala Glu Val Ala Ala Lys
            180                 185                 190

Ala Lys Ala Phe Val Glu Lys Ile Arg Gly Cys Thr Glu
        195                 200                 205

<210> SEQ ID NO 16

```
<211> LENGTH: 205
<212> TYPE: PRT
<213> ORGANISM: Artificial sequence
<220> FEATURE:
<223> OTHER INFORMATION: Synthetic sequence

<400> SEQUENCE: 16

Met Lys Met Glu Glu Leu Phe Lys Lys His Lys Ile Val Ala Val Leu
1               5                   10                  15

Arg Ala Asn Ser Val Glu Glu Ala Lys Met Lys Ala Leu Ala Val Phe
                20                  25                  30

Val Gly Gly Val His Leu Ile Glu Ile Thr Phe Thr Val Pro Asp Ala
            35                  40                  45

Asp Thr Val Ile Lys Glu Leu Ser Phe Leu Lys Glu Leu Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
        115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Ile Ala Glu Val Ala Ala Lys
            180                 185                 190

Ala Ala Ala Phe Val Gly Lys Ile Arg Gly Cys Thr Glu
        195                 200                 205

<210> SEQ ID NO 17
<211> LENGTH: 205
<212> TYPE: PRT
<213> ORGANISM: Artificial sequence
<220> FEATURE:
<223> OTHER INFORMATION: Synthetic sequence

<400> SEQUENCE: 17

Met Lys Met Glu Glu Leu Phe Lys Lys His Lys Ile Val Ala Val Leu
1               5                   10                  15

Arg Ala Asn Ser Val Glu Glu Ala Lys Met Lys Ala Leu Ala Val Phe
                20                  25                  30

Tyr Gly Gly Val His Leu Ile Glu Ile Thr Phe Thr Val Pro Asp Ala
            35                  40                  45

Asp Thr Val Ile Lys Glu Leu Ser Phe Leu Lys Glu Ala Gly Ala Ile
        50                  55                  60

Ile Gly Ala Gly Thr Val Thr Ser Val Glu Gln Cys Arg Lys Ala Val
65                  70                  75                  80

Glu Ser Gly Ala Glu Phe Ile Val Ser Pro His Leu Asp Glu Glu Ile
                85                  90                  95

Ser Gln Phe Cys Lys Glu Lys Gly Val Phe Tyr Met Pro Gly Val Met
            100                 105                 110

Thr Pro Thr Glu Leu Val Lys Ala Met Lys Leu Gly His Thr Ile Leu
```

```
            115                 120                 125

Lys Leu Phe Pro Gly Glu Val Val Gly Pro Gln Phe Val Lys Ala Met
    130                 135                 140

Lys Gly Pro Phe Pro Asn Val Lys Phe Val Pro Thr Gly Gly Val Asn
145                 150                 155                 160

Leu Asp Asn Val Cys Glu Trp Phe Lys Ala Gly Val Leu Ala Val Gly
                165                 170                 175

Val Gly Ser Ala Leu Val Lys Gly Thr Phe Val Glu Val Ala Ala Lys
            180                 185                 190

Ala Ala Ala Phe Val Glu Lys Ile Arg Gly Cys Thr Glu
            195                 200                 205

<210> SEQ ID NO 18
<211> LENGTH: 224
<212> TYPE: PRT
<213> ORGANISM: Artificial sequence
<220> FEATURE:
<223> OTHER INFORMATION: Synthetic sequence

<400> SEQUENCE: 18

Met His His His His His Gly Gly Ser Gly Gly Ser Gly Gly Ser
1               5                   10                  15

Gly Gly Ser Met Lys Met Glu Glu Leu Phe Lys Lys His Lys Ile Val
            20                  25                  30

Ala Val Leu Arg Ala Asn Ser Val Glu Glu Ala Lys Lys Lys Ala Leu
        35                  40                  45

Ala Val Phe Leu Gly Gly Val His Leu Ile Glu Ile Thr Phe Thr Val
    50                  55                  60

Pro Asp Ala Asp Thr Val Ile Lys Glu Leu Ser Phe Leu Lys Glu Met
65                  70                  75                  80

Gly Ala Ile Ile Gly Ala Gly Thr Val Thr Ser Val Glu Gln Cys Arg
                85                  90                  95

Lys Ala Val Glu Ser Gly Ala Glu Phe Ile Val Ser Pro His Leu Asp
            100                 105                 110

Glu Glu Ile Ser Gln Phe Cys Lys Glu Lys Gly Val Phe Tyr Met Pro
        115                 120                 125

Gly Val Met Thr Pro Thr Glu Leu Val Lys Ala Met Lys Leu Gly His
    130                 135                 140

Thr Ile Leu Lys Leu Phe Pro Gly Glu Val Val Gly Pro Gln Phe Val
145                 150                 155                 160

Lys Ala Met Lys Gly Pro Phe Pro Asn Val Lys Phe Val Pro Thr Gly
                165                 170                 175

Gly Val Asn Leu Asp Asn Val Cys Glu Trp Phe Lys Ala Gly Val Leu
            180                 185                 190

Ala Val Gly Val Gly Ser Ala Leu Val Lys Gly Thr Pro Val Glu Val
        195                 200                 205

Ala Glu Lys Ala Lys Ala Phe Val Glu Lys Ile Arg Gly Cys Thr Glu
    210                 215                 220

<210> SEQ ID NO 19
<211> LENGTH: 5
<212> TYPE: PRT
<213> ORGANISM: Artificial sequence
<220> FEATURE:
<223> OTHER INFORMATION: Synthetic sequence

<400> SEQUENCE: 19
```

```
Gly Ser Gly Ser Gly
1               5

<210> SEQ ID NO 20
<211> LENGTH: 10
<212> TYPE: PRT
<213> ORGANISM: Artificial sequence
<220> FEATURE:
<223> OTHER INFORMATION: synthetic sequence

<400> SEQUENCE: 20

Gly Gly Gly Gly Ser Gly Gly Gly Gly Ser
1               5                   10
```

US 11,452,771 B2

SCAFFOLDED HIV-1 ENV GP140 TRIMER IMMUNOGEN

CROSS-REFERENCE TO RELATED APPLICATIONS

The subject patent application is a divisional of U.S. patent application Ser. No. 16/177,165 (filed Oct. 31, 2018; now pending), which claims the benefit of priority to U.S. Provisional Patent Application No. 62/580,038 (filed Nov. 1, 2017). The full disclosure of the priority applications is incorporated herein by reference in its entirety and for all purposes.

STATEMENT OF GOVERNMENT SUPPORT

This invention was made with government support under grant numbers AI100663, AI084817, GM094586 and AI110657 awarded by The National Institutes of Health. The government has certain rights in the invention.

BACKGROUND OF THE INVENTION

Human immunodeficiency virus type-1 (HIV-1) is the primary cause of the acquired immune deficiency syndrome (AIDS). It can be divided into several different clades, for example A, B, C, D, E, F, G, H, J and K, which vary in prevalence throughout the world. Each clade comprises different strains of HIV-1 which have been grouped together on the basis of their genetic similarity. The envelope glycoprotein (Env) of HIV-1 harbors the epitopes of broadly neutralizing antibodies (bNAbs) and is the sole target of vaccine design. The cleaved, mature Env is presented on the HIV-1 virion surface as a metastable trimer of heterodimers each containing a (co-) receptor-binding protein, gp120, and a transmembrane protein, gp41, which anchors the trimeric spike in viral membrane and drives the fusion process during cell. Due to the labile nature and a dense layer of surface glycans, Env has long resisted structure determination and hampered trimer-based vaccine efforts.

Native-like Env trimers have recently been considered a desirable vaccine platform due to the promising successes achieved with the BG505 SOSIP.664 trimer. In addition to SOSIP, other trimer design platforms such as the single-chain gp140 (sc-gp140) trimer, native flexibly linked (NFL) trimer, and uncleaved prefusion-optimized (UFO) trimer were also proposed that produced native-like Env trimers. However, gp140 trimer may not be the optimal form of an HTV-1 vaccine because subunit vaccines are often less immunogenic than virus-like particles (VLPs), which present a dense array of antigens on the particle surface and induce potent, long-lasting immune responses upon vaccination.

Despite the increasing appreciation for the advantages of VLP vaccines in bNAb elicitation, the utility of nanoparticles as carriers to display native-like trimers has not been rigorously explored in HIV-1 vaccine development. There remains to be an unmet medical need for safe and efficacious HIV-1 vaccines. The present invention addresses this and other needs in the art.

SUMMARY OF THE INVENTION

In one aspect, the invention provides HIV-1 vaccine immunogens. The novel HIV-1 vaccine immunogens of the invention contain an HIV-1 Env-derived trimer protein presented on a self-assembling nanoparticle and also a T-helper epitope sequence. In some embodiments, the T-helper epitope links C-terminus of the HIV-1 trimer protein subunit to the N-terminus of the nanoparticle subunit. In some other embodiments, the T-helper epitope sequence is fused to the C-terminus of the nanoparticle subunit while C-terminus of the HIV-1 trimer protein is fused to the N-terminus of the nanoparticle subunit. In some of the latter embodiments, a short peptide spacer is used to fuse the T-helper epitope to the nanoparticle subunit. This allows formation of a hydrophobic core inside the nanoparticle, which functions to stabilize the nanoparticle structure and to promote T cell recognition of the fusion immunogen. In some of these embodiments, the employed short peptide spacer can be, e.g., 1-5 tandem repeats of GGGGS (SEQ ID NO:4) or GSGSG (SEQ ID NO:19), or any other peptide sequence that is structurally flexible by nature. In some of these embodiments, an additional short peptide segment or spacer can be used to fuse the HIV-1 protein to the N-terminus of the nanoparticle subunit, e.g., a 1G linker or any of the other short peptide spacers described herein. In some embodiments, the T-helper epitope sequence contains an amino acid sequence as shown in any one of SEQ ID NOs:1-3, a conservatively modified variant or a substantially identical sequence thereof.

Typically, the self-assembling nanoparticle in the HIV-1 vaccine immunogens is generated with a trimeric protein sequence. In some embodiments, the subunit of the self-assembling nanoparticle is (1) the polypeptide as shown in SEQ ID NO:18, a conservatively modified variant or a substantially identical sequence thereof, (2) the polypeptide as shown in any one of SEQ ID NOs:5-17, a conservatively modified variant or a substantially identical sequence thereof, (3) E2p or (4) ferritin.

In various embodiments, the HIV-1 Env-derived trimer protein in the vaccine immunogens of the invention is a gp140 trimer. In some embodiments, the employed HIV-1 Env-derived trimer protein is an uncleaved prefusion-optimized (UFO) gp140 trimer. In some of these embodiments, the UFO gp140 trimer is a chimeric trimer comprising a modified $gp41_{ECTO}$ domain from HIV-1 strain BG505. Some HIV-1 vaccine immunogens of the invention contain a HIV-1 Env-derived trimer that is an UFO gp140 trimer, a self-assembling nanoparticle that is generated with a subunit sequence as shown in any one of SEQ ID NOs:5-18, and a T-helper epitope that contains the sequence as shown in SEQ ID NO: 1.

In another aspect, the invention provides HIV-1 vaccine immunogens that contain an HIV-1 Env-derived trimer protein presented on a self-assembling nanoparticle that is formed with a subunit polypeptide as shown in any one of SEQ ID NOs:5-18, a conservatively modified variant or a substantially identical sequence thereof. In some embodiments, the employed HIV-1 Env-derived trimer protein is an uncleaved prefusion-optimized (UFO) gp140 trimer. In some of these embodiments, the UFO gp140 trimer is a chimeric trimer that contains a modified $gp41_{ECTO}$ domain from HIV-1 strain BG505. In some embodiments, the HIV-1 trimer protein in the HIV-1 vaccine immunogen is linked at its C-terminus to the N-terminus of the nanoparticle via a linker sequence. In some other embodiments, the linker sequence is fused to the C-terminus of the nanoparticle subunit via a short peptide spacer to form a hydrophobic core inside the nanoparticle while the UFO gp140 trimer subunit is fused to the N-terminus of the nanoparticle subunit. This functions to stabilize the nanoparticle structure and to promote T cell recognition of the trimer immunogen. In some of these embodiments, the employed short peptide spacer can be, e.g., GGGGS (SEQ ID NO:4), GSGSG (SEQ ID NO:19), or any other peptide that is structurally flexible by nature. In various embodiments, the employed linker sequence contains a T-helper epitope sequence or a glycine-serine linker. In some embodiments, the linker sequence contains the peptide sequence as shown in any one of SEQ ID NOs:1-3, a conservatively modified variant or a substantially identical sequence thereof. In some embodiments, the linker sequence contains 1 to 5 tandem repeats (e.g., 1 or 2 repeats) of GGGGS (SEQ ID NO:4) or GSGSG (SEQ ID NO:19). In some embodiments, an additional short peptide spacer or segment can be used to fuse the HIV-1 protein to the N-terminus of the nanoparticle subunit as exemplified herein.

In a related aspect, the invention provides pharmaceutical compositions that contain one of the novel scaffolded HIV-1 vaccine immunogens described herein. The pharmaceutical compositions typically also contain a pharmaceutically acceptable carrier. In some embodiments, the pharmaceutical compositions additionally contain an adjuvant. In another related aspect, the invention provides isolated or recombinant polynucleotides that encode the HIV-1 vaccine immunogens described herein, cloning and expression vectors harboring such polynucleotide sequences, as well as host cells into which the nucleic acids or vectors have been introduced or integrated.

In another aspect, the invention provides methods for preventing HIV-1 infection or eliciting an immune response against HIV-1 in a subject. These methods entail administering to the subject a therapeutically effective amount of one of the novel scaffolded HIV-1 vaccine immunogens described herein. Typically, the HIV-1 vaccine immunogen is administered to the subject via a pharmaceutical composition. In some embodiments, the administered HIV-1 vaccine immunogen contains an UFO gp140 trimer, a self-assembling nanoparticle generated with a subunit sequence as shown in SEQ ID NO:18, and a T-helper epitope sequence as shown in SEQ ID NO:1. In these embodiments, the T-helper epitope sequence functions to covalently link the UFO gp140 trimer at its C-terminus to the N-terminus of the nanoparticle subunit. Alternatively, the T-helper epitope sequence is fused to the C-terminus of the nanoparticle subunit via a short peptide spacer while the UFO gp140 trimer subunit is fused to the N-terminus of the nanoparticle subunit.

In another aspect, the invention provides methods for treating HIV-1 infection or eliciting an immune response against HIV-1 in a subject. The methods involve administering to the subject a pharmaceutical composition that contains a therapeutically effective amount of a HIV-1 vaccine immunogen described herein. In some embodiments, the administered HIV-1 vaccine immunogen contains an UFO gp140 trimer, a self-assembling nanoparticle generated with a subunit sequence as shown in SEQ ID NO:18, and a T-helper epitope sequence as shown in SEQ ID NO:1. In these methods, the T-helper epitope sequence functions to covalently link the UFO gp140 trimer at its C-terminus to the N-terminus of the nanoparticle subunit. Alternatively, the T-helper epitope sequence is fused to the C-terminus of the nanoparticle subunit via a short peptide spacer while the UFO gp140 trimer subunit is fused to the N-terminus of the nanoparticle subunit.

A further understanding of the nature and advantages of the present invention may be realized by reference to the remaining portions of the specification and claims.

DETAILED DESCRIPTION

I. Overview

Figure 1:
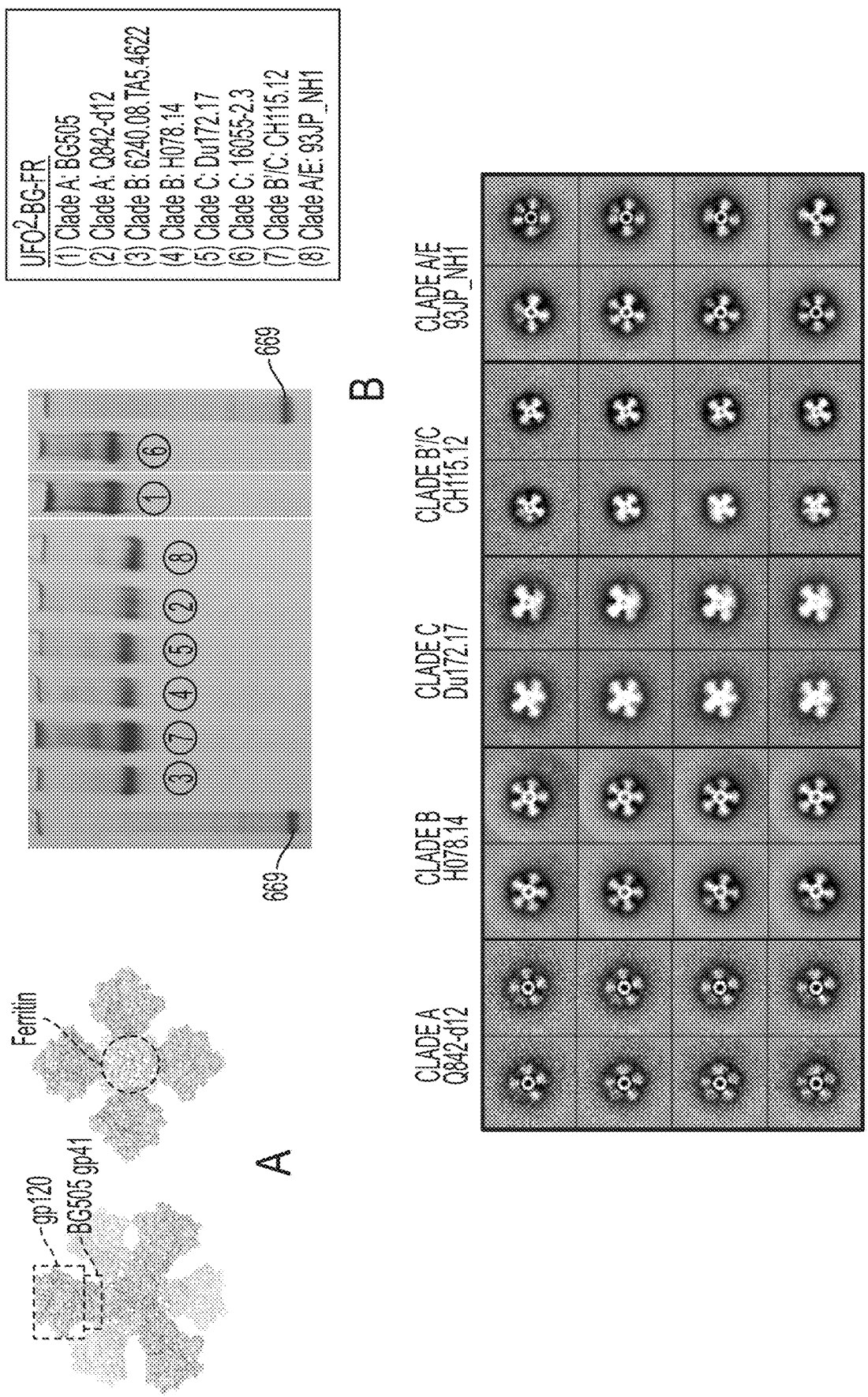
FIG. 1 shows ferritin nanoparticles presenting diverse UFO$^2$-BG trimers and I3-01-based gp140 nanoparticles with embedded T-help signal. (A) Surface model of UFO$^2$-BG gp140-ferritin (FR) nanoparticle, with gp120, BG505 gp41$_{ECTO}$ of the UFO design, and ferritin circled by dotted lines on the gp140-FR images and labeled with arrows. (B) BN-PAGE of eight UFO$^2$-BG-FR nanoparticles after a single-step 2G12 antibody affinity purification. (C) Reference-free 2D class averages derived from negative-stain EM of five representative UFO$^2$-BG-FR nanoparticles. (D) Antigenic profiles of five representative UFO$^2$-BG-FR nanoparticles against a small panel of six bNAbs and four non-NAbs. Sensorgrams were obtained from an Octet RED96 using an antigen titration series of six concentrations (starting at 35 nM by two-fold dilution). The peak values at the highest concentration are summarized in the matrix, in which six bNAbs and four non-NAbs are shown in upper and lower panels, respectively. Higher intensity of gray shade indicates greater binding signal measured by Octet. (E) Surface model of the I3-01 nanoparticle (light gray) is shown on the left, with the subunits surrounding a front-facing 5-fold axis highlighted in dark gray and three subunits forming a 3-fold axis marked with a black dotted-line triangle. The spacing between N-termini of three I3-01 subunits surrounding a 3-fold axis (top view) and the anchoring of a gp140 trimer onto three I3-01 subunits by flexible linkers (indicated by black dotted lines) are shown in the middle. Schematic representation of I3-01 nanoparticle constructs containing both gp140 and a T-helper epitope is shown on the right, with sequences listed for three such T-helper epitopes, PADRE, D, and TpD (SEQ ID NOs:1-3, respectively). (F) SEC profiles of three I3-01 nanoparticles presenting an HR1-redesigned BG505 gp140 trimer with different T-helper epitopes as linkers. (G) BN-PAGE of three abovementioned I3-01 nanoparticles after a single-step 2G12 affinity antibody purification. (H) Reference-free 2D class averages derived from negative-stain EM of an I3-01 nanoparticle presenting an HR1-redesigned BG505 gp140 trimer with PADRE used as a linker. (I) Antigenic profiles of gp140-PADRE-I3-01 nanoparticle against a small panel of six bNAbs and four non-NAbs. Sensorgrams were obtained from an Octet RED96 using an antigen titration series of six concentrations (starting at 14 nM by two-fold dilution). The six antigen concentrations, respectively corresponding to the six lines from top to bottom in each of the 10 antibody profiles, are indicated next to the PGT151 binding profile on the right.
Figure 1:
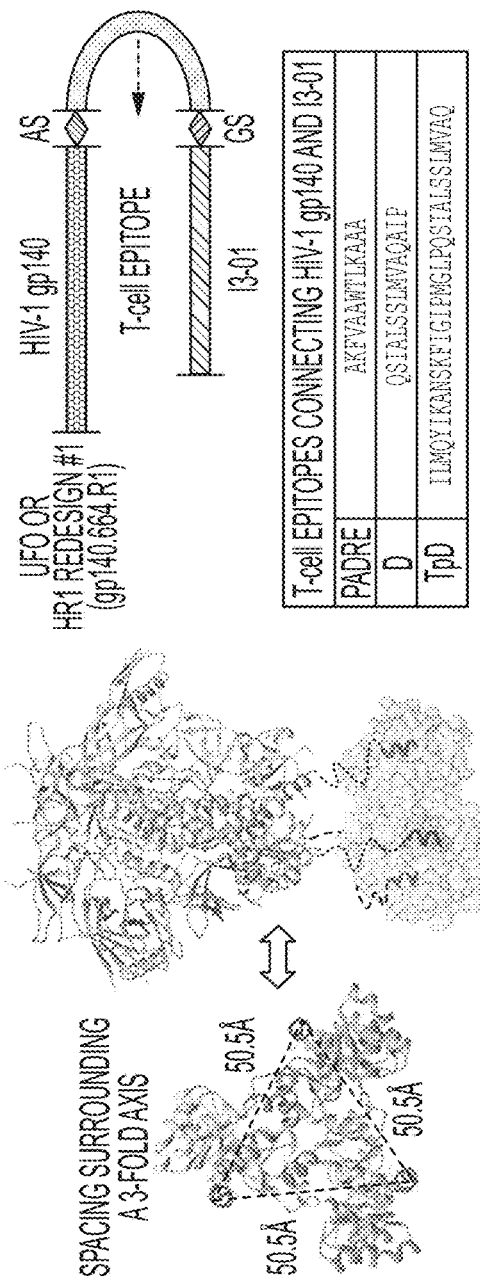
Figure 1:
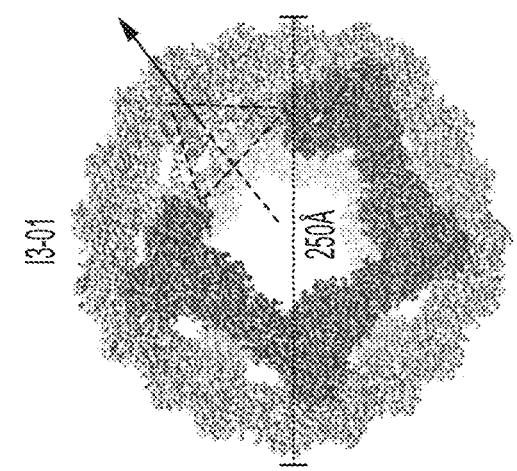
Figure 1:
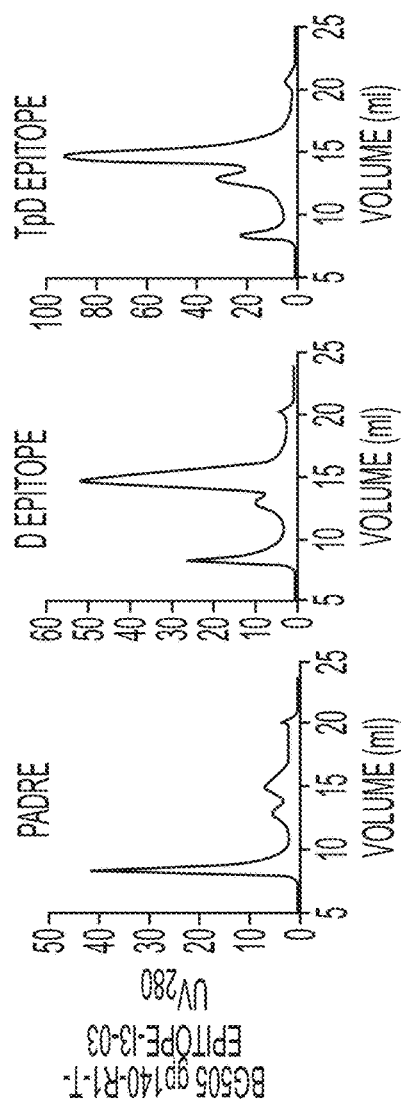
Figure 1:
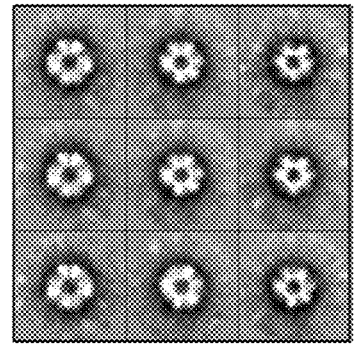
Figure 1:
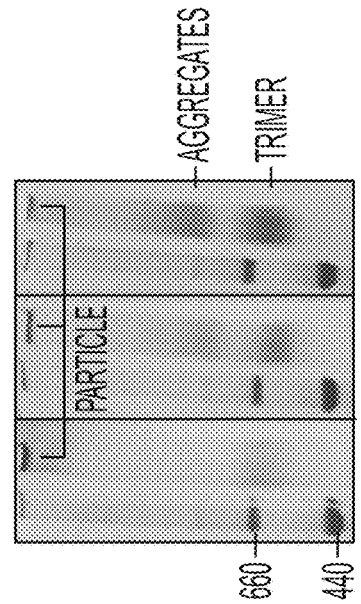
Figure 1:
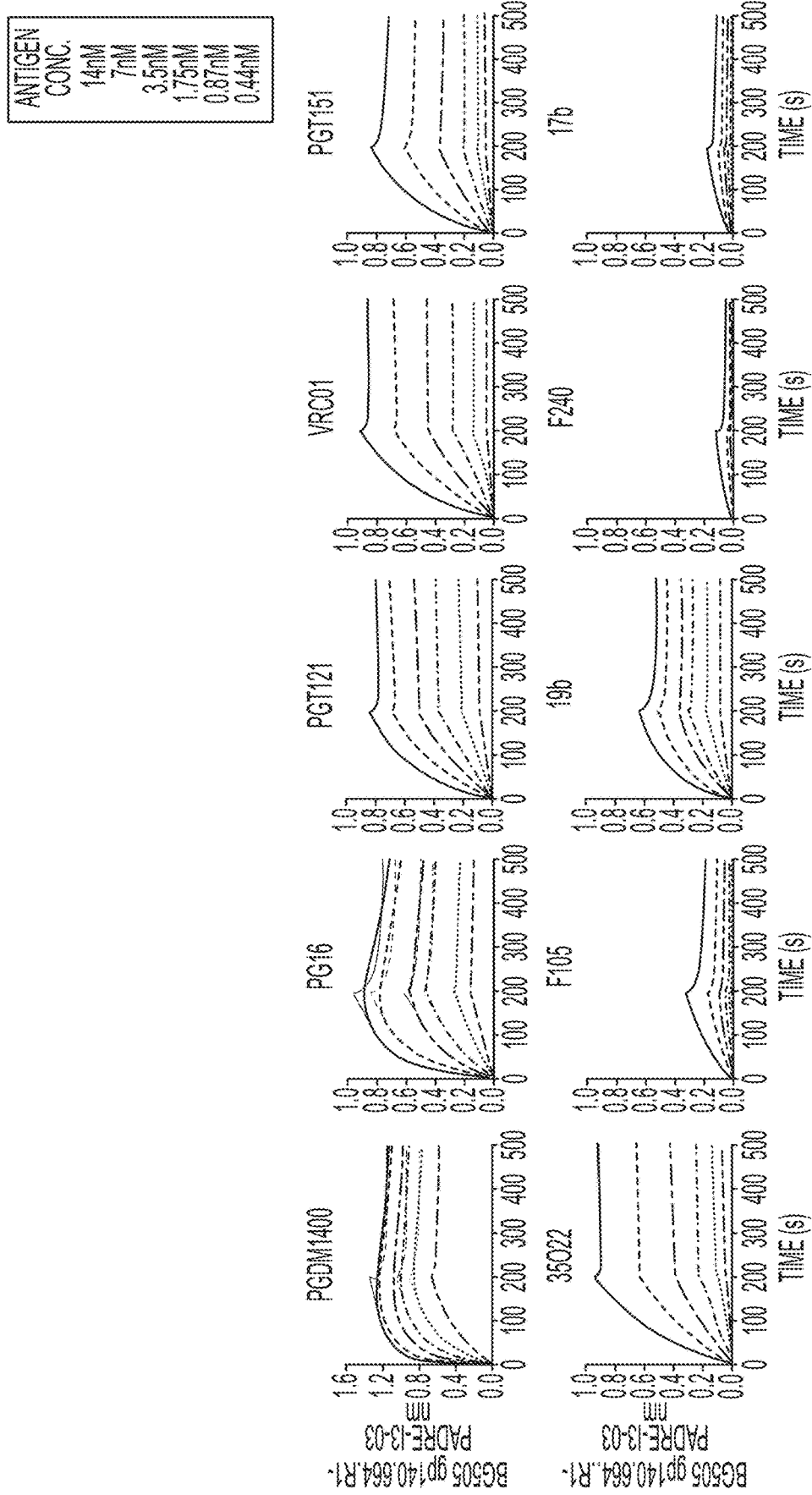

The present invention is predicated in part on the present inventors' development of novel HIV-1 gp140 nanoparticle immunogens. As detailed in the Examples herein, the inventors utilized a T-helper epitope that acts not only as the linker between gp140 and displaying nanoparticle scaffold, but also as an embedded T-help signal to induce robust T-cell responses and to steer B cell development towards bNAbs. The inventors additionally explored a previously unutilized protein (1VLW) to provide stable nanoparticle scaffold in presenting HIV-1 gp140 trimers. Upon purification with affinity column and size-exclusion chromatography, the various scaffolded HIV-1 gp140 immunogens display excellent purity and homogeneity. When evaluated with bNAbs and non-NAbs, the novel HIV-1 gp140 nanoparticles described herein exhibit an outstanding antigenic profile with a strong PG16 binding that has not been observed with other known HIV-1 gp140 nanoparticles. Further as exemplification, immunogenicity of the nanoparticles displaying a BG505 gp140 trimer was examined by immunizing mice and assessing HIV-1 neutralization activities of IgG isolated from the mice. Neutralization of autologous tier-2 BG505.N332 HIV-1 virus was observed for two HIV-1 gp140 nanoparticles disclosed herein (S2G5 and S2G6), as well as control HIV-1 immunogens (a scaffolded gp140.681 trimer (S1G5) and a ferritin nanoparticle (S2G1)). Importantly, the novel HIV-1 gp140 nanoparticle immunogens described herein yielded an IC50 value indicative of rapid development of tier-2 NAbs after only 8 weeks of immunization, presenting the best HIV-1 vaccine candidate identified thus far, with balanced T- and B-cell responses.

The invention accordingly provides novel scaffolded HIV-1 vaccine immunogens harboring a T-helper epitope as exemplified herein. Also provided in the invention are scaffolded HIV-1 vaccine immunogens containing stable nanoparticle formed with 1VLW variants. The invention additionally provides therapeutic and preventive applications of these novel scaffolded HIV-1 immunogens in the treatment or prevention of HIV-1 infections.

Unless otherwise specified herein, the vaccine immunogens of the invention, the encoding polynucleotides, expression vectors and host cells, as well as the related therapeutic applications, can all be generated or performed in accordance with the procedures exemplified herein or routinely practiced methods well known in the art. See, e.g., Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954; Sambrook et al., Molecular Cloning: A Laboratory Manual, Cold Spring Harbor Press, N.Y., ($3^{rd}$ ed., 2000); Brent et al., Current Protocols in Molecular Biology, John Wiley & Sons, Inc. (ringbou ed., 2003); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998). The following sections provide additional guidance for practicing the compositions and methods of the present invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press ($1^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons ($3^{rd}$ ed., 2002); *Dictionary of Chemistry*, Hunt (Ed.), Routledge ($1^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press ($4^{th}$ ed., 2000). Further clarifications of some of these terms as they apply specifically to this invention are provided herein.

As used herein, the singular forms "a," "an," and "the," refer to both the singular as well as plural, unless the context clearly indicates otherwise. For example, "an Env-derived trimer" can refer to both single or plural Env-derived trimer molecules, and can be considered equivalent to the phrase "at least one Env-derived trimer."

Unless otherwise noted, the terms "antigen" and "immunogen" are used interchangeably to refer to a substance, typically a protein, which is capable of inducing an immune response in a subject. The terms also refer to proteins that are immunologically active in the sense that once administered to a subject (either directly or by administering to the subject a nucleotide sequence or vector that encodes the protein) is able to evoke an immune response of the humoral and/or cellular type directed against that protein. Thus, in some embodiments, the term "immunogen" can broadly encompass polynucleotides that encode polypeptide or protein antigens described herein.

The term "conservatively modified variant" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Epitope refers to an antigenic determinant. These are particular chemical groups or peptide sequences on a molecule that are antigenic, such that they elicit a specific immune response, for example, an epitope is the region of an antigen to which B and/or T cells respond. Epitopes can be formed both from contiguous amino acids or noncontiguous amino acids juxtaposed by tertiary folding of a protein.

Effective amount of a vaccine or other agent that is sufficient to generate a desired response, such as reduce or eliminate a sign or symptom of a condition or disease, such as AIDS. For instance, this can be the amount necessary to inhibit viral replication or to measurably alter outward symptoms of the viral infection, such as increase of T cell counts in the case of an HIV-1 infection. In general, this amount will be sufficient to measurably inhibit virus (for example, HIV) replication or infectivity. When administered to a subject, a dosage will generally be used that will achieve target tissue concentrations (for example, in lymphocytes) that has been shown to achieve in vitro inhibition of viral replication. In some examples, an "effective amount" is one that treats (including prophylaxis) one or more symptoms and/or underlying causes of any of a disorder or disease, for example to treat HIV. In one example, an effective amount is a therapeutically effective amount. In one example, an effective amount is an amount that prevents one or more signs or symptoms of a particular disease or condition from developing, such as one or more signs or symptoms associated with AIDS.

Ferritin is a globular protein found in all animals, bacteria, and plants. It acts primarily to control the rate and location of polynuclear $Fe(III)_2O_3$ formation through the transportation of hydrated iron ions and protons to and from a mineralized core. The globular form of ferritin is made up of monomeric subunit proteins (also referred to as monomeric ferritin subunits), which are polypeptides having a molecule weight of approximately 17-20 kDa.

As used herein, a fusion protein is a recombinant protein containing amino acid sequence from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment(s) (e.g., inside a cell). For example, the amino acid sequences of monomeric subunits that make up ferritin, and the amino acid sequences of HIV-1 gp120 or gp41 glycoproteins are not normally found joined together via a peptide bond.

HIV-1 envelope protein (Env) is initially synthesized as a longer precursor protein of 845-870 amino acids in size, designated gp160. gp160 forms a homotrimer and undergoes glycosylation within the Golgi apparatus. In vivo, gp160 glycoprotein is endo-proteolytically processed to the mature envelope glycoproteins gp120 and gp41, which are noncovalently associated with each other in a complex on the surface of the virus. The gp120 surface protein contains the high affinity binding site for human CD4, the primary receptor for HIV, as well as domains that interact with fusion coreceptors, such as the chemokine receptors CCR5 and CXCR4. The gp41 protein spans the viral membrane and contains at its amino-terminus a sequence of amino acids important for the fusion of viral and cellular membranes. The native, fusion-competent form of the HIV-1 envelope glycoprotein complex is a trimeric structure composed of three gp120 and three gp41 subunits. The receptor-binding (CD4 and co-receptor) sites are located in the gp120 moieties, whereas the fusion peptides are located in the gp41 components. Exemplary sequence of wildtype gp160 polypeptides are shown in GenBank, e.g., under accession numbers AAB05604 and AAD12142.

gp140 refers to an oligomeric form of HIV envelope protein, which contains all of gp120 and the entire gp41 ectodomain. As used herein, a HIV-1 gp140 trimer immunogen typically contains a gp140 domain and a modified or redesigned ectodomain of gp140 ($gp41_{ECTO}$).

gp120 is an envelope protein of the Human Immunodeficiency Virus (HIV). gp120 contains most of the external, surface-exposed, domains of the HIV envelope glycoprotein complex, and it is gp120 which binds both to cellular CD4 receptors and to cellular chemokine receptors (such as CCR5). The mature gp120 wildtype polypeptides have about 500 amino acids in the primary sequence. Gp120 is heavily N-glycosylated giving rise to an apparent molecular weight of 120 kD. The polypeptide is comprised of five conserved regions (C1-05) and five regions of high variability (V1-V5). In its tertiary structure, the gp120 glycoprotein is comprised of three major structural domains (the outer domain, the inner domain, and the bridging sheet) plus the variable loops. See, e.g., Wyatt et al., Nature 393, 705-711, 1998; and Kwong et al., Nature 393, 649-59, 1998. The inner domain is believed to interact with the gp41 envelope glycoprotein, while the outer domain is exposed on the assembled envelope glycoprotein trimer.

Variable region 1 and Variable Region 2 (V1/V2 domain) of gp120 are comprised of about 50-90 residues which contain two of the most variable portions of HIV-1 (the V1 loop and the V2 loop), and one in ten residues of the V1/V2 domain are N-glycosylated.

gp41 is a proteolytic product of the precursor HIV envelope protein. It contains an N-terminal fusion peptide (FP), a transmembrane domain, as well as an ectodomain that links the fusion peptide and a transmembrane domain. gp41 remains in a trimeric configuration and interacts with gp120 in a non-covalent manner. The amino acid sequence of an exemplary gp41 is set forth in GenBank, under Accession No. CAD20975.

BG505 SOSIP.664 gp140 is a HIV-1 Env immunogen developed with the gp140 trimer from clade-A strain BG505. It contains a covalent linkage between the cleaved gp120 and gp41$_{ECTO}$ with an engineered disulfide bond (termed SOS). In addition, it has an I559P mutation (termed IP) to destabilize the gp41 post-fusion conformation and also a truncation of the membrane-proximal external region (MPER) at residue 664 to improve solubility. This HIV-1 immunogen has an outstanding antigenic profile and excellent structural mimicry of the native spike. Using the SOSIP trimer as a sorting probe, new bNAbs have been identified and characterized. The SOSIP design has also been extended to other HIV-1 strains and permitted the incorporation of additional stabilizing mutations. Recently, immunogenicity of SOSIP trimers in rabbits and nonhuman primates was reported, paving the way for human vaccine trials.

Immune response refers to a response of a cell of the immune system, such as a B cell, T cell, or monocyte, to a stimulus. In some embodiment, the response is specific for a particular antigen (an "antigen-specific response"). In some embodiments, an immune response is a T cell response, such as a CD4+ response or a CD8+ response. In some other embodiments, the response is a B cell response, and results in the production of specific antibodies.

Immunogenic composition refers to a composition comprising an immunogenic polypeptide that induces a measurable CTL response against virus expressing the immunogenic polypeptide, or induces a measurable B cell response (such as production of antibodies) against the immunogenic polypeptide.

Sequence identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Homologs or orthologs of nucleic acid or amino acid sequences possess a relatively high degree of sequence identity/similarity when aligned using standard methods. Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The term "subject" refers to any animal classified as a mammal, e.g., human and non-human mammals. Examples of non-human animals include dogs, cats, cattle, horses, sheep, pigs, goats, rabbits, and etc. Unless otherwise noted, the terms "patient" or "subject" are used herein interchangeably. Preferably, the subject is human.

The term "treating" or "alleviating" includes the administration of compounds or agents to a subject to prevent or delay the onset of the symptoms, complications, or biochemical indicia of a disease (e.g., an HIV infection), alleviating the symptoms or arresting or inhibiting further development of the disease, condition, or disorder. Subjects in need of treatment include those already suffering from the disease or disorder as well as those being at risk of developing the disorder. Treatment may be prophylactic (to prevent or delay the onset of the disease, or to prevent the manifestation of clinical or subclinical symptoms thereof) or therapeutic suppression or alleviation of symptoms after the manifestation of the disease.

Uncleaved pre-fusion-optimized (UFO) trimers refer to HIV-1 gp140 trimeric proteins that are formed with gp120 protein and a redesigned gp41$_{ECTO}$ domain, which results in more stabilized HIV-1 gp140 trimers. The redesigned gp41$_{ECTO}$ domain is based on the prototype HIV-1 strain BG505 (and the prototype gp140 trimer BG505 SOSIP.664 gp140) and contains one or more modifications relative to the wildtype BG505 gp41$_{ECTO}$ sequence. These modifications include (1) replacement of the 21 residue N-terminus of HR1 (residues 548-568) with a shorter loop sequence to stabilize the pre-fusion gp140 structure and (2) replacement of the furin cleavage site between gp120 and gp41 (residues 508-511) with a flexible linker sequence such a tandem repeat of a GGGGS (SEQ ID NO:4) motif. In some embodiments, the UFO trimer can additionally contain an engineered disulfide bond between gp120 and gp41 and/or a stabilizing mutation in gp41. For example, UFO trimers based on HIV-1 strain BG505 can contain an engineered disulfide bond is between residues A501C and T605C, and/or a stabilizing mutation I559P. Detailed description of UFO trimers is provided in, e.g., Kong et al., Nat. Comm. 7:12040, 2016. In addition to UFO trimers based on the BG505 strain sequence, the engineered gp41$_{ECTO}$ domain can be used to pair with a gp120 polypeptide from many different HIV-1 strains or subtypes to form "chimeric" gp140 trimers. Such chimeric trimers are termed "UFO-BG" or "UFO$^2$-BG" as exemplified herein.

Vaccine refers to a pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents.

Virus-like particle (VLP) refers to a non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) Biophys. J. 60:1445-1456; and Hagensee et al. (1994) J. Virol. 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

III. Novel Scaffolded HIV-1 Trimer Immunogens

The invention provides HIV-1 immunogens that contain a heterologous scaffold that presents or incorporates a trimeric HIV-1 Env-derived protein (e.g., gp140 trimer) and also a T-helper or linker sequence. In some embodiments, the heterologous presenting scaffold is a self-assembling nanoparticle. In some other embodiments, the heterologous presenting scaffold is a virus-like particle (VLP) such as bacteriophage $Q_\beta$ VLP. In some embodiments (as exemplified in Example 1 herein), subunit of the trimeric HIV-1 protein is linked to the N-terminus of the subunit of the displaying scaffold (e.g., nanoparticle) via a linker sequence described herein, e.g., a T-helper epitope polypeptide that also functions to promote T cell recognition of the fusion immunogen. In some other embodiments (as exemplified in Example 7 herein), subunit of the HIV-1 trimer protein is connected (e.g., covalently linked) to the N-terminus of subunit of the displaying scaffold, and a T-helper or linker epitope is fused to the C-terminus of subunit of the displaying scaffold (e.g., nanoparticle). In the latter embodiments, the T-helper epitope can be fused to the nanoparticle subunit via a short peptide spacer. This allows the formation of a hydrophobic core inside the nanoparticle that functions to stabilize the nanoparticle structure and to promote T cell recognition of the fusion immunogen. In various embodiments, the short peptide spacer can be, e.g., 1-5 repeats of GGGGS (SEQ ID NO:4), GSGSG (SEQ ID NO:19), or any peptide that is structurally flexible by nature. As exemplification, T-helper epitope PADRE can be fused to the C-terminus of the subunit of E2p and I3-01 with a 5-aa GGGGS (SEQ ID NO:4) spacer (Example 7). In addition to using a short peptide spacer to fuse the T-helper epitope to the C-terminus of the nanoparticle subunit, a second peptide spacer or segment can be used to fuse the HIV-1 trimer to the N-terminus of the nanoparticle subunit. For example, the HIV-1 protein can be fused to the N-terminus of the displaying nanoparticle subunit via, e.g., a single glycine residue ("1G linker") or 10-aa GGGGSGGGGS (SEQ ID NO:20) spacer exemplified herein (Example 7).

Any Env-derived HIV-1 trimer proteins can be used in the nanoparticle-presented vaccine compositions. The Env-derived trimer protein can be obtained from various HIV-1 strains. In some embodiments, the nanoparticles present a native trimeric form of HIV-1 Env based glycoproteins or domains, e.g., gp140, gp120 or V1V2 domains. In some embodiments, the Env-derived trimer is from HIV-1 strain BG505, e.g., the BG505. SOSIP.664 gp140 trimer. In some embodiments, the nanoparticles present a modified gp140 trimer immunogen, e.g., a HR1-modified gp140 trimer ("UFO trimer") described in Kong et al., Nat. Comm. 7, 12040, 2016. In some embodiments, the HIV-1 trimeric immunogen used in the invention is a UFO$^2$-BG trimer as exemplified herein. UFO$^2$-BG trimers are chimeric gp140 trimers containing (1) the BG505 gp41 domain with a redesigned HR1 N-terminal bend and a cleavage-site linker (as described in Kong et al., Nat. Comm. 7, 12040, 2016) and (2) the gp120 protein from one of other diverse HIV-1 strains or subtypes. In addition to the redesigned gp41$_{ECTO}$ domain from the BG505 strain, the gp41 domain in the chimeric gp140 trimers suitable for the invention can also be a consensus gp41$_{ECTO}$ domain derived from the HIV-1 sequence database.

In various embodiments, nanoparticle displaying any of these HIV-1 Env-derived immunogens can be constructed by fusing the trimer immunogen to the subunit of the nanoparticle (e.g., I3-01, 1VLW derived polypeptide sequences or ferritin subunit). The antigenicity and structural integrity of these nanoparticle based HIV-1 immunogens can be readily analyzed via standard assays, e.g., antibody binding assays and negative-stain electron microscopy (EM). As exemplified herein, the various fusion molecules can all self-assemble into nanoparticles that display immunogenic epitopes of the Env-derived trimer (e.g., gp140). By eliciting a robust trimer-specific bnAbs, these nanoparticles are useful for vaccinating individuals against a broad range of HIV-1 viruses.

In some embodiments, the scaffolded gp140 trimer immunogens of the invention contain a T-helper epitope that functions as a linker to connect the gp140 trimer to the nanoparticle scaffold. In some other embodiments, the T-helper epitope is fused to the C-terminus of the nanoparticle subunit via a short peptide spacer and is encapsulated inside the nanoparticle scaffold. The short peptide spacer that can be employed in these embodiments can be, e.g., GGGGS (SEQ ID NO:4), GSGSG (SEQ ID NO:19), or any other peptide that is structurally flexible by nature. In addition to its role as a structural element of the scaffolded immunogen, the T-helper epitope also provides an embedded T-help signal to induce robust T-cell responses and to steer B cell development towards bNAbs. Any T-helper epitope sequences or peptides known in the art may be employed in the practice of the present invention. They include any polypeptide sequence that contain MHC class-II epitopes and can effectively activate helper T cells upon immunization. See, e.g., Alexander et al., Immunity 1, 751-761, 1994; Ahlers et al., J. Clin. Invest. 108:1677-1685, 2001; Fraser et al., Vaccine 32, 2896-2903, 2014; De Groot et al., Immunol. Cell Biol. 8:255-269, 2002; and Gene Ther. 21: 225-232, 2014. In some preferred embodiments, the employed T-helper epitope is a universal pan DR epitope peptide (PADRE). In some of these embodiments, the linker contains a sequence AKFVAAWTLKAAA (SEQ ID NO:1), a conservatively modified variant or substantially identical (e.g., at least 90%, 95% or 99% identical) sequence thereof. In some other embodiments, the employed T-helper epitope is the D T-helper epitope QSIALSSLMVAQAIP (SEQ ID NO:2) or the TpD epitope ILMQYIKANSKFIGIPMGLPQ-SIALSSLMVAQ (SEQ ID NO:3). In various embodiments, the linker can contain a sequence as shown in SEQ ID NO:2 or SEQ ID NO:3, a substantially identical (e.g., at least 90%, 95% or 99% identical) sequence or a conservatively substituted sequence thereof.

As noted above, the heterologous scaffold for presenting or displaying the trimeric HIV-1 protein is preferably a nanoparticle. Various nanoparticle platforms can be employed in generating the vaccine compositions of the invention. In general, the nanoparticles employed in the invention need to be formed by multiple copies of a single subunit. Additionally or alternatively, the amino-terminus of the particle subunit has to be exposed and in close proximity to the 3-fold axis, and the spacing of three amino-termini has to closely match the spacing of the carboxyol-termini of various HIV-1 trimeric components. In some preferred embodiments, the immunogens comprise self-assembling nanoparticles with a diameter of about 20 nm or less (usually assembled from 12, 24, or 60 subunits) and 3-fold axes on the particle surface. Such nanoparticles provide suitable particle platforms to produce multivalent HIV-1 trimer vaccines.

In some embodiments, the scaffolded gp140 trimer immunogens of the invention are constructed with a hyperstable nanoparticle scaffold. For example, the self-assembly nanoparticle can be generated with the I3-01 protein described in Hsia et al., Nature 535, 136-139, 2016. The amino acid sequence of this protein is shown in SEQ ID NO:18. In some other embodiments, the hyperstable nanoparticle scaffold may be based on a variant of I3-01 as described in Hsia et al. (supra), including a conservatively modified variant or one with a substantially identical (e.g., at least 90%, 95% or 99% identical) sequence. In some embodiments, the linker sequence for connecting the gp140 trimer to the I3-01 derived nanoparticle platform contains a T-helper epitope as described above. In some other embodiments, a glycine-serine polypeptide is used as a second peptide spacer for connecting the gp140 trimer to the I3-01 derived nanoparticle platform, and a T-helper epitope is fused to the C-terminus of the nanoparticle subunit via a short peptide spacer. Such a structural design leads to the creation of a hydrophobic core inside the nanoparticle, which enhances T-cell recognition of the gp140 trimer displayed on the nanoparticle surface. In various embodiments, the short peptide spacer for linking the T-helper epitope to the C-terminus of the nanoparticle subunit can be, e.g., GGGGS (SEQ ID NO:4), GSGSG (SEQ ID NO:19), or any other peptide that is structurally flexible by nature.

I3-01 sequence (SEQ ID NO: 18):
MHHHHHHGGSGGSGGSGGSMKMEELFKKHKIVAVLRANSVEEAKKKA

LAVFLGGVHLIEITFTVPDADTVIKELSFLKEMGAIIGAGTVTSVEQ

CRKAVESGAEFIVSPHLDEEISQFCKEKGVFYMPGVMTPTELVKAMK

LGHTILKLFPGEVVGPQFVKAMKGPFPNVKFVPTGGVNLDNVCEWFK

AGVLAVGVGSALVKGTPVEVAEKAKAFVEKIRGCTE

In some embodiments, the hyperstable nanoparticles in the scaffolded gp140 trimer immunogens of the invention are constructed with ferritin, a natural nanoparticle from *Helicobacter pylori*. For example, the scaffolded gp140 trimer immunogens can contain a UFO²-BG trimer that is linked to and presented on ferritin. In some of these embodiments, the UFO2-BG trimer is directly connected to the ferritin subunit without a linker sequence, as exemplified herein. In some other embodiments, a linker sequence such as a T-helper epitope or a simple glycine-serine linker may be used. In some of these embodiments, a T-helper epitope can be fused to the C-terminus of a nanoparticle subunit via a short peptide spacer, which results in the formation of a hydrophobic core within the nanoparticle scaffold. As described herein, the short peptide spacer used in these embodiments can be, e.g., GGGGS (SEQ ID NO:4), GSGSG (SEQ ID NO:19), or any other peptide that is structurally flexible by nature. Ferritin is a globular protein found in all animals, bacteria, and plants. The globular form of ferritin is made up of monomeric subunit proteins (also referred to as monomeric ferritin subunits), which are polypeptides having a molecule weight of approximately 17-20 kDa. A monomeric ferritin subunit used in the invention is a full length, single polypeptide of a ferritin protein, or any portion thereof, which is capable of directing self-assembly of monomeric ferritin subunits into the globular form of the protein. Amino acid sequences from monomeric ferritin subunits of any known ferritin protein can be used to produce fusion proteins of the present invention, so long as the monomeric ferritin subunit is capable of self-assembling into a nanoparticle displaying HIV-1 epitopes on its surface. In addition to ferritin, the invention can also employ many other self-assembling nanoparticles with similar molecular traits. These include, e.g., molecules with the following PDB IDs: 1JIG (12-mer Dlp-2 from *Bacillus anthracis*), 1UVH (12-mer DPS from *Mycobacterium smegmatis*), 2YGD (24-mer eye lens chaperone αB-crystallin), 3CS0 (24-mer DegP24), 3MH6 and 3MH7 (24-mer HtrA proteases), 3PV2 (12-mer HtrA homolog DegQ WT), 4A8C (12-mer DegQ from *E. coli*.), 4A9G (24-mer DegQ from *E. coli*.), 4EVE (12-mer HP-NAP from *Helicobacter pylori* strain YS29), and 4GQU (24-mer HisB from *Mycobacterium tuberculosis*).

In some embodiments, the scaffolded gp140 trimer immunogens of the invention can be constructed with a nanoparticle scaffold that is derived from protein 1VLW (SEQ ID NO:5) or its variants as exemplified herein (SEQ ID NOs: 6-17). In various embodiments, the nanoparticle platform for constructing the scaffolded gp140 immunogens of the invention can be produced with a polypeptide sequence that is a conservatively modified variant or a substantially identical sequence of any one of SEQ ID NOs:5-18. In some embodiments, the linker sequence for connecting the gp140 trimer to the 1VLW derived nanoparticle platform contains a T-helper epitope as described above. In some other embodiments, the linker for connecting the gp140 trimer to the 1VLW derived nanoparticle platform contains a simple peptide sequence. For example, the scaffolded immunogens can be constructed with a glycine-serine linker, e.g., a linker that contains 1 to 5 repeats (e.g., 1 or 2 repeats) of GGGGS (SEQ ID NO:4) or GSGSG (SEQ ID NO:19). In some other embodiments, a T-helper epitope can be fused to the C-terminus of the nanoparticle subunit via a short peptide spacer to form a hydrophobic core inside the nanoparticle. In various embodiments, the employed short peptide spacer can be, e.g., GGGGS (SEQ ID NO:4), GSGSG (SEQ ID NO: 19), or any other peptide that is structurally flexible by nature.

In some other embodiments, the nanoparticle scaffold for presenting HIV-1 trimer immunogens are redesigned variants of dihydrolipoyl acyltransferase (E2p) from *Bacillus stearothermophilus*. E2p is a thermostable 60-meric nanoparticle with a diameter of 23.2 nm and 12 large openings separating the threefold vertices on the particle surface. Nanoparticles formed with the redesigned E2p variants for constructing the scaffolded HIV-1 trimer immunogens of the invention have enhanced stability relative to the wildtype E2p nanoparticles. In some embodiments, the HIV-1 gp140 trimer can be connected to E2p nanoparticle with a linker that contains a T-helper epitope described above. In some other embodiments, a T-helper epitope can be fused to the C-terminus of the E2p subunit via a short peptide spacer so that the fully assembled E2p nanoparticle encapsulate a hydrophobic core formed by the T-helper epitope. The hydrophobic core also functions to enhance the T-cell recognition of the gp140 trimer on the E2p nanoparticle surface. The short peptide spacer suitable for use in these embodiments for linking E2p and the T-helper epitope can be, e.g., GGGGS (SEQ ID NO:4), GSGSG (SEQ ID NO:19), or any other peptide that is structurally flexible by nature.

The scaffolded HIV-1 trimer immunogens of the invention can be constructed in accordance with the protocols described herein (e.g., Examples 1-7) and/or other methods that have been described in the art, e.g., He et al., Nat. Comm. 7, 12041, 2016; and Kong et al., Nat. Comm. 7, 12040, 2016.

IV. Vectors and Host Cells for Expressing HIV-1 Vaccine Immunogens

The invention provides polynucleotide sequences that encode the HIV-1 vaccine immunogens and related polypeptides as described herein, expression vectors that harbor the polynucleotide sequences, as well as host cells that harbor the polynucleotides or expression constructs. The cell can be, for example, a eukaryotic cell, or a prokaryotic cell, such as an animal cell, a plant cell, a bacterium, or a yeast. A variety of expression vector/host systems are suitable for expressing the fusion polypeptides of the invention. Examples include, e.g., microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vector (e.g., cauliflower mosaic virus, CaMV; tobacco mosaic virus, TMV) or transformed with bacterial expression vectors (e.g., Ti or pBR322 plasmid); or animal cell systems.

Vectors useful for the invention preferably contain sequences operably linked to the fusion polypeptide coding sequences that permit the transcription and translation of the encoding polynucleotide sequences. Sequences that permit the transcription of the linked fusion polypeptide encoding sequences include a promoter and optionally also include an enhancer element or elements permitting the strong expression of the linked sequences. The term "transcriptional regulatory sequences" refers to the combination of a promoter and any additional sequences conferring desired expression characteristics (e.g., high level expression, inducible expression, tissue- or cell-type-specific expression) on an operably linked nucleic acid sequence. The promoter sequence can be constitutive or inducible. Examples of constitutive viral promoters include the HSV, TK, RSV, SV40 and CMV promoters. Examples of suitable inducible promoters include promoters from genes such as cytochrome P450 genes, heat shock protein genes, metallothionein genes, hormone-inducible genes, such as the estrogen gene promoter, and the like.

In addition to promoter/enhancer elements, expression vectors of the invention may further comprise a suitable terminator. Such terminators include, for example, the human growth hormone terminator, or, for yeast or fungal hosts, the TPI1 (Alber & Kawasaki, J Mol Appl Genet. 1:419-34, 1982) or ADH3 terminator (McKnight et al., 1985, EMBO J. 4: 2093-2099). Vectors useful for the invention may also comprise polyadenylation sequences (e.g., the SV40 or Ad5E1b poly(A) sequence), and translational enhancer sequences (e.g., those from Adenovirus VA RNAs). Further, a vector useful for the invention may encode a signal sequence directing the fusion polypeptide to a particular cellular compartment or, alternatively, may encode a signal directing secretion of the fusion polypeptide.

In some preferred embodiments, vectors expressing the vaccine immunogens of the invention are viral vectors for mammalian expression. In general, any viral vector that permits the introduction and expression of sequences encoding the fusion HIV-immunogens of the invention is acceptable for the invention. In various embodiments, mammalian expression vectors can be used in the practice of the invention, including the adenoviral vectors, the pSV and the pCMV series of plasmid vectors, vaccinia and retroviral vectors, as well as baculovirus. For example, the HIV-1 vaccine immunogens of the invention can be expressed from viral vector phCMV3.

Depending on the specific vector used for expressing the fusion polypeptide, various known cells or cell lines can be employed in the practice of the invention. The host cell can be any cell into which recombinant vectors carrying a fusion HIV-immunogen of the invention may be introduced and wherein the vectors are permitted to drive the expression of the fusion polypeptide is useful for the invention. It may be prokaryotic, such as any of a number of bacterial strains, or may be eukaryotic, such as yeast or other fungal cells, insect or amphibian cells, or mammalian cells including, for example, rodent, simian or human cells. Cells expressing the fusion polypeptides of the invention may be primary cultured cells, for example, primary human fibroblasts or keratinocytes, or may be an established cell line, such as NIH3T3, HEK293, HEK293T HeLa, MDCK, WI38, or CHO cells. In some embodiments, the host cells for expressing the HIV-1 vaccine immunogens of the invention can be ExpiCHO cells or HEK293F cells as exemplified herein. The skilled artisans can readily establish and maintain a chosen host cell type in culture that expresses the fusion vaccine immunogens of the invention. Many other specific examples of suitable cell lines that can be used in expressing the fusion polypeptides are described in the art. See, e.g., Smith et al., 1983, J. Virol 46:584; Engelhard, et al., 1994, Proc Nat Acad Sci 91:3224; Logan and Shenk, 1984, Proc Natl Acad Sci, 81:3655; Scharf, et al., 1994, Results Probl Cell Differ, 20:125; Bittner et al., 1987, Methods in Enzymol, 153:516; Van Heeke & Schuster, 1989, J Biol Chem 264:5503; Grant et al., 1987, Methods in Enzymology 153:516; Brisson et al., 1984, Nature 310:511; Takamatsu et al., 1987, EMBO J 6:307; Coruzzi et al., 1984, EMBO J 3:1671; Broglie et al., 1984, Science, 224:838; Winter J and Sinibaldi R M, 1991, Results Probl Cell Differ., 17:85; Hobbs S or Murry L E in McGraw Hill Yearbook of Science and Technology (1992) McGraw Hill New York N.Y., pp 191-196 or Weissbach and Weissbach (1988) Methods for Plant Molecular Biology, Academic Press, New York, pp 421-463.

The fusion polypeptide-expressing vectors may be introduced to selected host cells by any of a number of suitable methods known to those skilled in the art. For the introduction of fusion polypeptide-encoding vectors to mammalian cells, the method used will depend upon the form of the vector. For plasmid vectors, DNA encoding the fusion polypeptide sequences may be introduced by any of a number of transfection methods, including, for example, lipid-mediated transfection ("lipofection"), DEAE-dextran-mediated transfection, electroporation or calcium phosphate precipitation. These methods are detailed, for example, in Brent et al., supra. Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies) or LipoTaxi™ (Stratagene) kits are available. Other companies offering reagents and methods for lipofection include Bio-Rad Laboratories, CLONTECH, Glen Research, InVitrogen, JBL Scientific, MBI Fermentas, PanVera, Promega, Quantum Biotechnologies, Sigma-Aldrich, and Wako Chemicals USA.

For long-term, high-yield production of recombinant fusion polypeptides, stable expression is preferred. Rather than using expression vectors which contain viral origins of replication, host cells can be transformed with the fusion polypeptide-encoding sequences controlled by appropriate expression control elements (e.g., promoter, enhancer, sequences, transcription terminators, polyadenylation sites, etc.), and selectable markers. The selectable marker in the recombinant vector confers resistance to the selection and allows cells to stably integrate the vector into their chromosomes. Commonly used selectable markers include neo, which confers resistance to the aminoglycoside G-418 (Colberre-Garapin, et al., J. Mol. Biol., 150:1, 1981); and hygro, which confers resistance to hygromycin (Santerre, et al., Gene, 30: 147, 1984). Through appropriate selections, the transfected cells can contain integrated copies of the fusion polypeptide encoding sequence.

V. Pharmaceutical Compositions and Therapeutic Applications

The invention provides pharmaceutical compositions and related methods of using the scaffolded HIV-1 immunogen polypeptides or polynucleotides encoding the vaccine polypeptides described herein for preventing and treating HIV-1 infections. In some embodiments, the immunogens disclosed herein are included in a pharmaceutical composition. The pharmaceutical composition can be either a therapeutic formulation or a prophylactic formulation. Typically, the composition additionally includes one or more pharmaceutically acceptable vehicles and, optionally, other therapeutic ingredients (for example, antibiotics or antiviral drugs). Various pharmaceutically acceptable additives can also be used in the compositions.

Some of the pharmaceutical compositions of the invention are vaccines. For vaccine compositions, appropriate adjuvants can be additionally included. Examples of suitable adjuvants include, e.g., aluminum hydroxide, lecithin, Freund's adjuvant, MPL™ and IL-12. In some embodiments, the scaffolded HIV-1 immunogens disclosed herein can be formulated as a controlled-release or time-release formulation. This can be achieved in a composition that contains a slow release polymer or via a microencapsulated delivery system or bioadhesive gel. The various pharmaceutical compositions can be prepared in accordance with standard procedures well known in the art. See, e.g., Remington's Pharmaceutical Sciences, 19.sup.th Ed., Mack Publishing Company, Easton, Pa., 1995; Sustained and Controlled Release Drug Delivery Systems, J. R. Robinson, ed., Marcel Dekker, Inc., New York, 1978); U.S. Pat. Nos. 4,652,441 and 4,917,893; 4,677,191 and 4,728,721; and 4,675,189.

Pharmaceutical compositions of the invention can be readily employed in a variety of therapeutic or prophylactic applications for treating HIV-1 infection or eliciting an immune response to HIV-1 in a subject. For example, the composition can be administered to a subject to induce an immune response to HIV-1, e.g., to induce production of broadly neutralizing antibodies to HIV-1. For subjects at risk of developing an HIV infection, a vaccine composition of the invention can be administered to provide prophylactic protection against viral infection. Depending on the specific subject and conditions, pharmaceutical compositions of the invention can be administered to subjects by a variety of administration modes known to the person of ordinary skill in the art, for example, intramuscular, subcutaneous, intravenous, intra-arterial, intra-articular, intraperitoneal, or parenteral routes. In general, the pharmaceutical composition is administered to a subject in need of such treatment for a time and under conditions sufficient to prevent, inhibit, and/or ameliorate a selected disease or condition or one or more symptom(s) thereof. The immunogenic composition is administered in an amount sufficient to induce an immune response against HIV-1. For therapeutic applications, the compositions should contain a therapeutically effective amount of the scaffolded HIV-1 immunogen described herein. For prophylactic applications, the compositions should contain a prophylactically effective amount of the scaffolded HIV-1 immunogen described herein. The appropriate amount of the immunogen can be determined based on the specific disease or condition to be treated or prevented, severity, age of the subject, and other personal attributes of the specific subject (e.g., the general state of the subject's health and the robustness of the subject's immune system). Determination of effective dosages is additionally guided with animal model studies followed up by human clinical trials and is guided by administration protocols that significantly reduce the occurrence or severity of targeted disease symptoms or conditions in the subject.

For prophylactic applications, the immunogenic composition is provided in advance of any symptom, for example in advance of infection. The prophylactic administration of the immunogenic compositions serves to prevent or ameliorate any subsequent infection. Thus, in some embodiments, a subject to be treated is one who has, or is at risk for developing, an HIV infection, for example because of exposure or the possibility of exposure to HIV. Following administration of a therapeutically effective amount of the disclosed therapeutic compositions, the subject can be monitored for HIV-1 infection, symptoms associated with HIV-1 infection, or both.

For therapeutic applications, the immunogenic composition is provided at or after the onset of a symptom of disease or infection, for example after development of a symptom of HIV-1 infection, or after diagnosis of HIV-1 infection. The immunogenic composition can thus be provided prior to the anticipated exposure to HIV virus so as to attenuate the anticipated severity, duration or extent of an infection and/or associated disease symptoms, after exposure or suspected exposure to the virus, or after the actual initiation of an infection.

The pharmaceutical composition of the invention can be combined with other agents known in the art for treating or preventing HIV infections. These include, e.g., antibodies or other antiviral agents such as nucleoside reverse transcriptase inhibitors, such as abacavir, AZT, didanosine, emtricitabine, lamivudine, stavudine, tenofovir, zalcitabine, zidovudine, and the like, non-nucleoside reverse transcriptase inhibitors, such as delavirdine, efavirenz, nevirapine, protease inhibitors such as amprenavir, atazanavir, indinavir, lopinavir, nelfinavir, osamprenavir, ritonavir, saquinavir, tipranavir, and the like, and fusion protein inhibitors such as enfuvirtide and the like. Administration of the pharmaceutical composition and the known anti-HIV agents can be either concurrently or sequentially.

The HIV-1 vaccine immunogens or pharmaceutical compositions of the invention can be provided as components of a kit. Optionally, such a kit includes additional components including packaging, instructions and various other reagents, such as buffers, substrates, antibodies or ligands, such as control antibodies or ligands, and detection reagents. An optional instruction sheet can be additionally provided in the kits.

EXAMPLES

The following examples are offered to illustrate, but not to limit the present invention.

Example 1 Design and Characterization of UFO²-BG Trimers

A major obstacle faced by current trimer designs is the deterioration of yield, purity, and stability once they are extended from BG505 to other strains. The solutions proposed thus far include (1) purification methods aimed to separate native-like trimers from misfolded Env proteins, such as bNAb affinity columns, negative selection, multi-cycle SEC, and a combined chromatographic approach; and (2) auxiliary mutations informed by atomic structures or derived from library screening. However, these solutions are empirical by nature and often result in suboptimal outcomes such as reduced trimer yield and unexpected change in Env properties. We previously identified an HR1 bend (residues 547-569) as the primary cause of Env metastability (Kong et al., Nat. Comm. 7, 12040, 2016). Rational redesign of this structurally strained region in $gp41_{ECTO}$ significantly improved trimer yield and purity for multiple HIV-1 strains, yet still produced varying amounts of misfolded Env, suggesting that other regions besides HR1 also contribute to Env metastability. Thus, uncovering the source of these 'secondary factors of metastability' may prove crucial to trimer design.

We hypothesized that all factors of Env metastability are encoded within $gp41_{ECTO}$, and that BG505 $gp41_{ECTO}$ of the UFO design (termed UFO²-BG) can be used to stabilize diverse HIV-1 Envs. To examine this hypothesis, we selected ten Envs of five clade origins (A, B, C, B/C, and A/E) from either a large panel of HIV-1 pseudoviruses or the available database, and also included three Envs tested in our previous study (Kong et al., Nat. Comm. 7, 12040, 2016). Of note, seven of the ten Envs tested here were derived from tier-2/3 isolates, posing a significant challenge to trimer stabilization. For each Env, the gp140 constructs of SOSIP, UFO, and UFO²-BG designs were expressed transiently in ExpiCHO cells, with furin co-transfected for the SOSIP construct. Following GNL purification, the SEC profiles of thirty gp140s were generated from a Superdex 200 16/600 column for comparison. With the exception of BG505, all SOSIPs showed a significant proportion of aggregates (40-50 ml), which was accompanied by extremely low yield and sometimes absence of the trimer peak. UFOs notably improved the trimer yield and purity except for clade A/E, with the most visible improvement observed for clade C. UFO²-BG demonstrated outstanding trimer purity and yield for eight of ten strains with no or slight hints of dimers and monomers, covering all seven tier-2/3 isolates. All thirty gp140 constructs were then characterized by BN-PAGE. Overall, UFO²-BG dramatically reduced the dimer and monomer contents with respect to SOSIP and UFO, showing a trimer band across SEC fractions, but occasionally with a faint band of lower molecular weight. Based on this finding, we compared the total Env protein obtained from a GNL column against the trimer portion after subsequent SEC and fraction analysis by BN-PAGE. Surprisingly, a simple step of GNL purification yielded comparable purity for all but two UFO²-BG trimers derived from a tier-2 clade-B strain and a tier-3 clade-B/C strain. Next, thermal stability was assessed for eight purified UFO²-BG trimers by differential scanning calorimetry (DSC). Notably, the DSC profiles exhibited a clade/strain-specific pattern, with the thermal denaturation midpoint ($T_m$) ranging from 60.9 to 68.4° C. Among the eight trimers tested, BG505—for which UFO-BG is equivalent to UFO—yielded the highest $T_m$ (68.4° C.), which was followed by two clade-C trimers (65.2-66.2° C.). In the absence of additional cavity-filling mutations and disulfide bonds, the DSC data reflected, in large part, the thermal stability of WT Envs. Of note, the CN54 UFO and UFO-BG constructs tested here contains 14 mutations (CN54M14), which reduce aggregates for 293 F-produced trimers. In addition, four UFO²-BG trimers of clades B, C, and B/C were selected for expression in 293 F cells and SEC purification. The results indicate that UFO²-BG can improve trimer properties irrespective of the cell lines used but only reach the highest purity when used in conjunction with the ExpiCHO system, consistent with our finding for BG505.

The results thus confirm our hypothesis that $gp41_{ECTO}$ is the sole source of Env metastability and BG505 $gp41_{ECTO}$ of the UFO design can stabilize diverse HIV-1 Envs. The nearly identical trimer purity prior to and following the SEC purification suggests a simple, robust, and cost-effective manufacturing process for the UFO²-BG trimers. The inherent trimer purity will also accelerate the development and clinical testing of nucleic acid vaccines expressing the UFO²-BG trimers.

Example 2 Nanoparticle Presentation of UFO²-BG Trimers from Diverse Subtypes Following our previously reported design strategy (He et al., Nat. Comm. 7, 12041, 2016), we investigated whether the UFO²-BG trimers derived from diverse HIV-1 strains can be displayed on the 24-meric ferritin (FR) nanoparticle. We hypothesize that BG505 $gp41_{ECTO}$ of the UFO design can facilitate both gp140 trimerization and nanoparticle assembly (FIG. 1A). To test this hypothesis, we designed eight UFO²-BG-FR constructs with the C terminus of $gp41_{ECTO}$ (residue 664) fused to the N terminus (Asp5) of a ferritin subunit. The resulting fusion constructs were expressed transiently in ExpiCHO cells followed by a simple purification using the 2G12 affinity column. BN-PAGE displayed a distinctive band of high molecular weight corresponding to well-formed UFO²-BG-FR nanoparticles for all eight strains studied. Consistently, nanoparticle assembly was confirmed by negative-stain EM, showing a visible particle core decorated with a regular array of gp140 trimers protruding from the surface. The DSC analysis indicated high thermal stability for UFO²-BG-FR nanoparticles derived from all five subtypes, with $T_m$ ranging from 68 to 70° C. The antigenicity of UFO²-BG-FR nanoparticles was assessed for five representative designs using a panel of six bNAbs and four non-NAbs. Overall, multivalent display has retained, and in some cases enhanced, the native-like trimer antigenicity, showing patterns specific to the epitopes as well as subtypes. For the V2 apex, all five nanoparticles bound to PGDM1400 with comparable or notably higher affinity than individual trimers, confirming that trimers displayed on nanoparticle surface adopt native-like, closed conformations. For H078.14, the restored bNAb binding could be explained by a shift of conformational equilibrium influenced by neighboring trimers on the nanoparticle surface, whereas for Du172.17 and 93JP_NH1 the increased affinity was likely a result of avidity effect. By contrast, little improvement was observed for nanoparticle binding to another apex bNAb, PG16. For the N332 supersite and CD4bs, multivalent display exhibited a more favorable effect on the H078.14 UFO²-BG trimer. For the gp120-gp41 interface, while all UFO²-BG-FR nanoparticles retained their trimer binding to PGT151, which recruits elements of two adjacent gp140 protomers, a cross-clade reduction of binding signal was observed for 35022, which interacts with only one protomer. For non-NAbs, nanoparticles exhibited binding profiles resembling those of trimers.

We next examined the utility of a 60-unit hyperstable nanoparticle, I3-01 (Hsia et al., Nature 535, 136-139, 2016), for multivalent display of native-like Env trimers. In terms of symmetry (dodecahedron) and size (25 nm), I3-01 closely resembles the 60-meric E2p nanoparticle tested in our previous study, but with greater stability (FIG. 1E, left). However, the large spacing between the N termini of I3-01 subunits, ~50.5 Å, requires a long linker to connect with the C termini of the gp140 trimer (FIG. 1E, middle). We hypothesize that a T-helper epitope may be used not only as a linker between gp140 and an I3-01 subunit but also as an embedded T-help signal to induce robust T-cell responses and to steer B cell development towards bNAbs. To test this hypothesis, a Pan DR epitope peptide (PADRE), AKFVAAWTLKAAA (SEQ ID NO:1) (Alexander et al., Immunity 1, 751-761, 1994) and two more recently reported T-helper epitopes, D and TpD (Fraser et al., Vaccine 32, 2896-2903, 2014), were selected for evaluation (FIG. 1E, right). Three fusion constructs were designed that contain the HR1-redesigned BG505 gp140 (Kong et al., Nat. Comm. 7, 12040, 2016), a T-helper epitope, and the I3-01 subunit. Following furin co-expression in ExpiCHO cells, the 2G12-purified material was characterized by SEC (FIG. 1F). Remarkably, the I3-01 construct that contains PADRE produced high-purity nanoparticles, as further confirmed by BN-PAGE (FIG. 1G) and negative-stain EM (FIG. 1h). When evaluated using the same panel of bNAbs and non-NAbs, this nanoparticle exhibited an outstanding antigenic profile with a strong PG16 binding that has not been observed for any nanoparticles tested thus far (FIG. 1I).

In summary, our results demonstrate that the UFO²-BG trimers of diverse HIV-1 strains can be displayed on ferritin nanoparticle. In addition, the use of a hyperstable nanoparticle such as I3-01 and a T-helper epitope provide a novel platform for developing multivalent HIV-1 vaccines with more balanced T and B cell responses.

Example 3 Nanoparticles Potently Activate B Cells Expressing bNAbs

Figure 2:
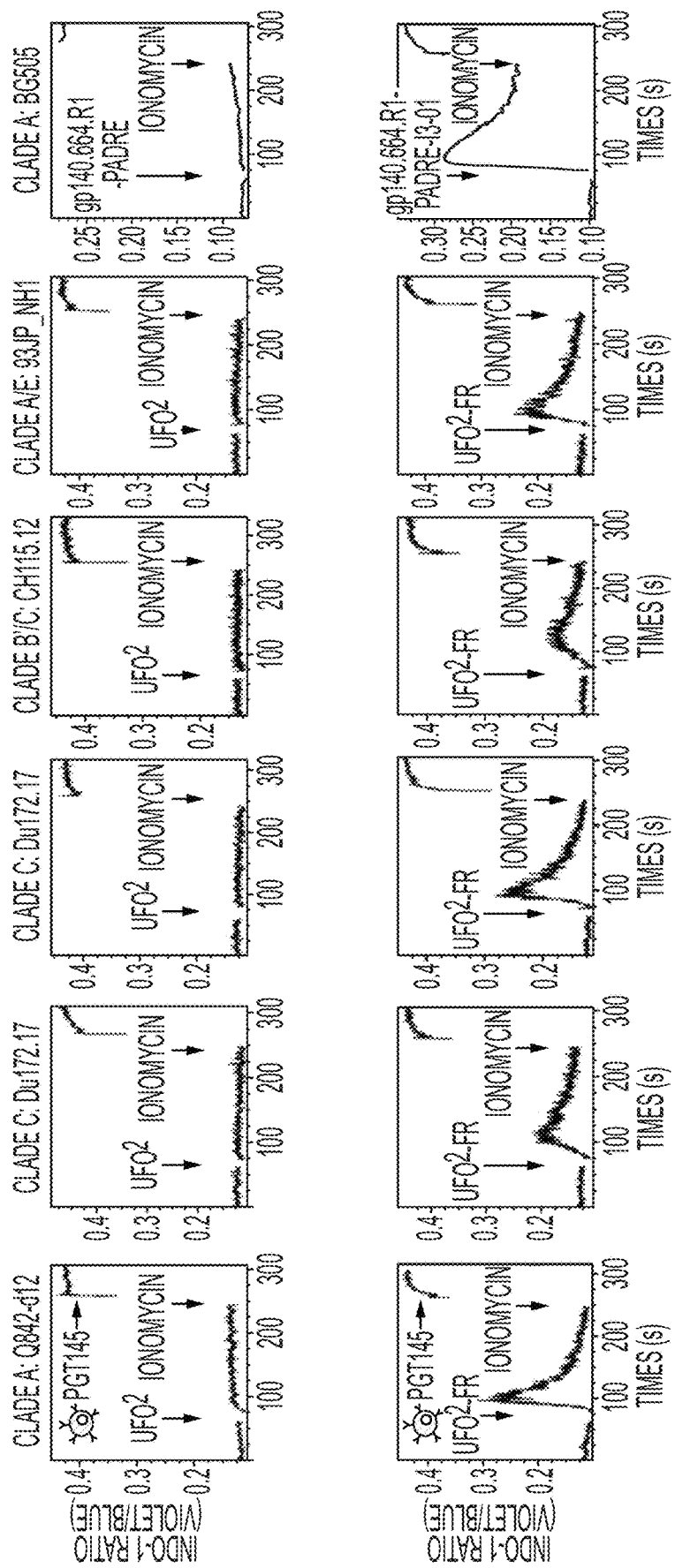
FIG. 2 shows effective B cell activation by trimer-presenting nanoparticles. Ca$^{2+}$ mobilization in B cell transfectants carrying (A) PGT145, (B) PGT121, and (C) VRC01 receptors. WEHI231 cells expressing a doxycyclin-inducible form of bNAb B cell receptor (BCR) were stimulated with anti-BCR antibodies or the indicated antigens at a concentration of 10 μg ml$^{-1}$: anti-human Ig κ-chain F(ab')$_2$; anti-mouse IgM; an UFO$^2$-BG-FR nanoparticle derived from a clade-A, B, C, B/C, or A/E strain, or BG505 gp140-PADRE-I3-01 nanoparticle containing a redesigned HR1 bend within gp41$_{ECTO}$.
Figure 2:
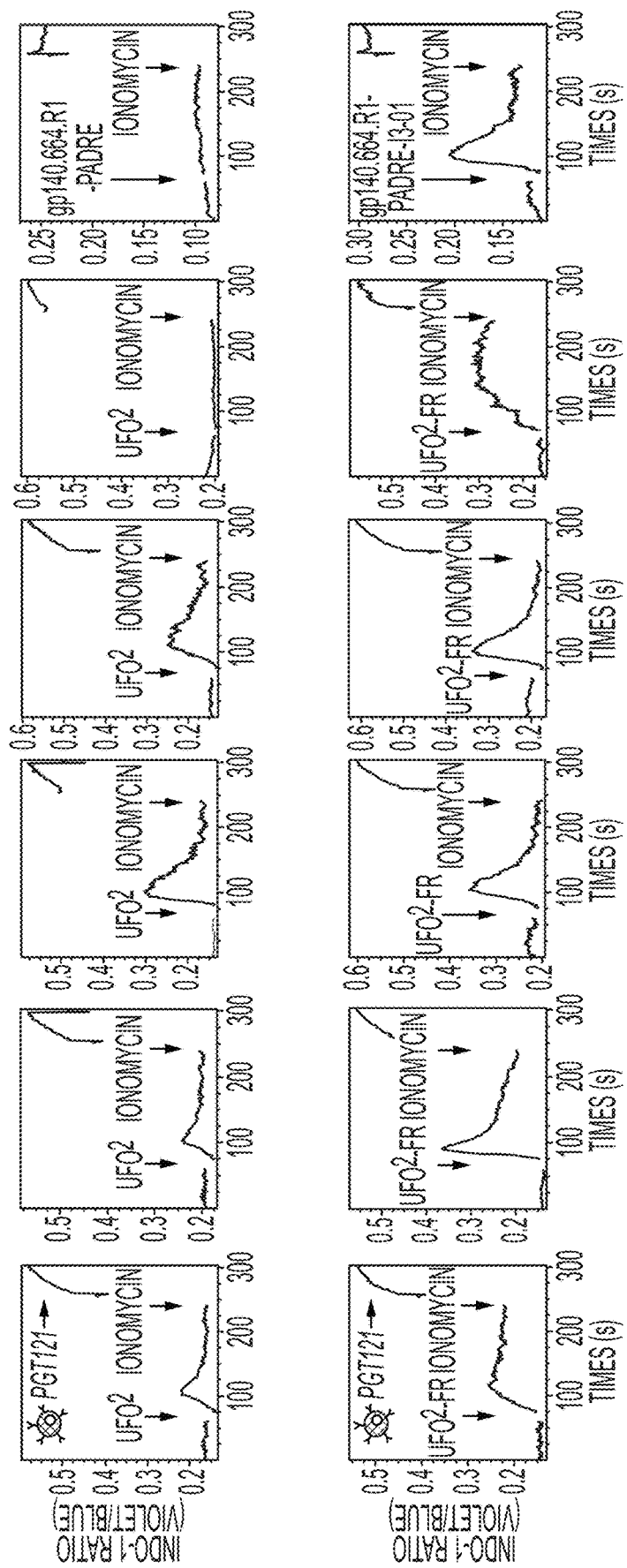
Figure 2:
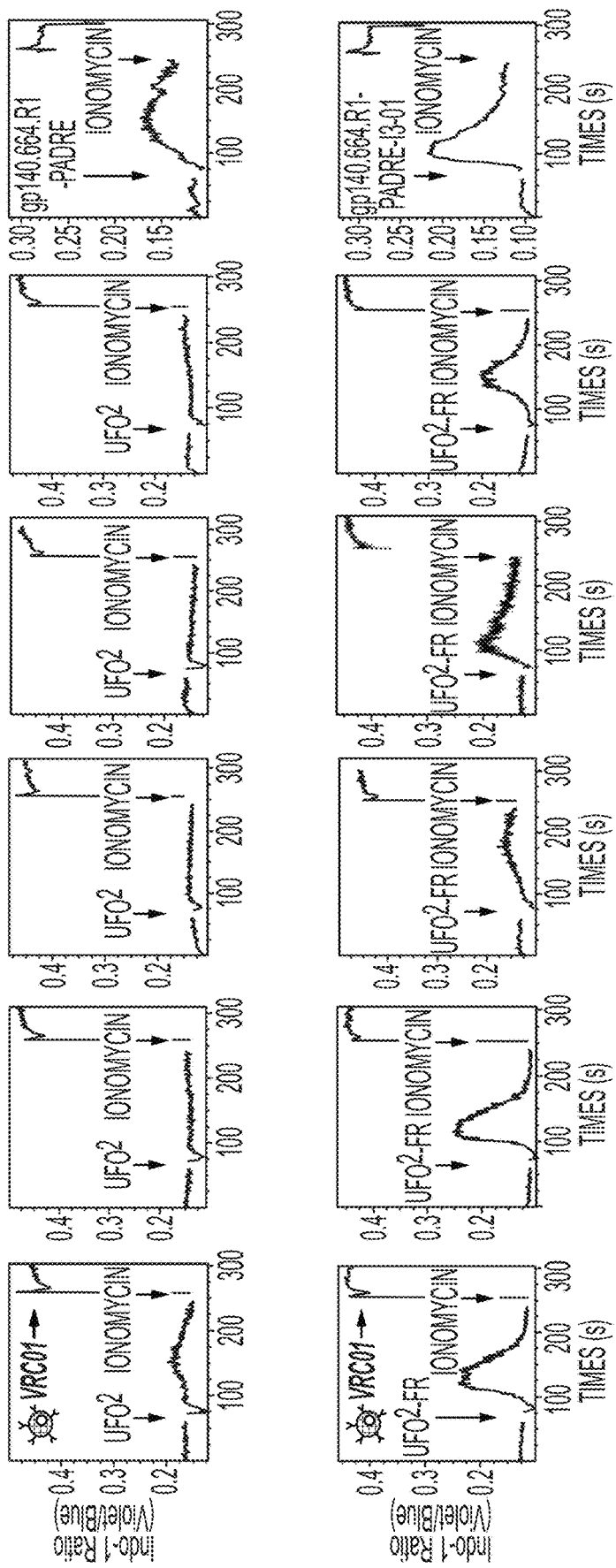

Previously, we demonstrated that various BG505 gp120 and gp140 nanoparticles could engage B cells expressing cognate VRC01 receptors (He et al., 2016). In this study, we assessed the B cell activation by five UFO²-BG-FR nanoparticles and a BG505 gp140-PADRE-I3-01 nanoparticle with respect to individual trimers (FIG. 2). B cells expressing bNAbs PGT145, VRC01, and PGT121 (Ota et al., J. Immunol. 189, 4816-4824, 2012) were used in the assay. Overall, trimer-presenting nanoparticles could stimulate bNAb-expressing B cells more effectively than individual trimers, with peak signals approaching the maximal activation by ionomycin. However, the results also revealed a pattern pertinent to the epitope examined: when tested in B cells expressing PGT145, which recognize the N332 supersite, some trimers and all nanoparticles rendered detectable $Ca^{2+}$ flux signals; by contrast, none and few trimers activated B cells expressing PGT145 and VRC01, which target the V2 apex and the CD4bs, respectively. Of note, the stimulation of PGT145-expressing B cells by the H078.14 UFO²-BG-FR nanoparticle provides further evidence that the apex can be restored by multivalent display without V2 mutation, consistent with the BLI data (FIG. 1D). A similar effect was also observed for the clade-A/E 93JP_NH1 UFO²-BG-FR nanoparticle, which bound to PGT121 only weakly by BLI but induced a visible, long-lasting $Ca^{2+}$ flux signal in PGT121-expressing B cells, suggesting that cross-linking of B cell receptors (BCRs) on cell surface may offer additional help to overcome the inherent low affinity. Together, by combining biochemical, structural, and antigenic approaches with B cell activation assays, we established a panel of gp140 nanoparticles that should permit investigation of their vaccine potential in vivo.

Example 4 Induction of Autologous Neutralizing Antibodies in Wildtype Mice

Immunogenicity has been assessed for various forms of native-like Env trimers. When wild-type mice were immunized with SOSIP trimers, no autologous tier-2 NAb response to BG505.N332 was observed over a period of eighteen weeks (Hu et al., J. Virol. 89, 10383-10398, 2015). It was concluded that the glycan shield of well-formed Env trimers is impenetrable for murine antibodies due to their short heavy-chain complementarity-determining region 3 (HCDR3) loops. Nonetheless, tier-2 NAbs were reported to be elicited by modified BG505 SOSIP trimers in mice with knock-in bNAb precursors. Using vaccination regimens spanning six months to one year, native-like trimers were also reported to induce an autologous tier-2 NAb response in rabbits and a weaker such response in macaques (de Taeye et al., 2015; Klasse et al., 2016; Martinez-Murillo et al., 2017; Pauthner et al., 2017; Sanders et al., 2015). Therefore, the induction of tier-2 NAbs remains a significant challenge to HIV-1 vaccine development, particularly in the WT mouse model.

Figure 3:
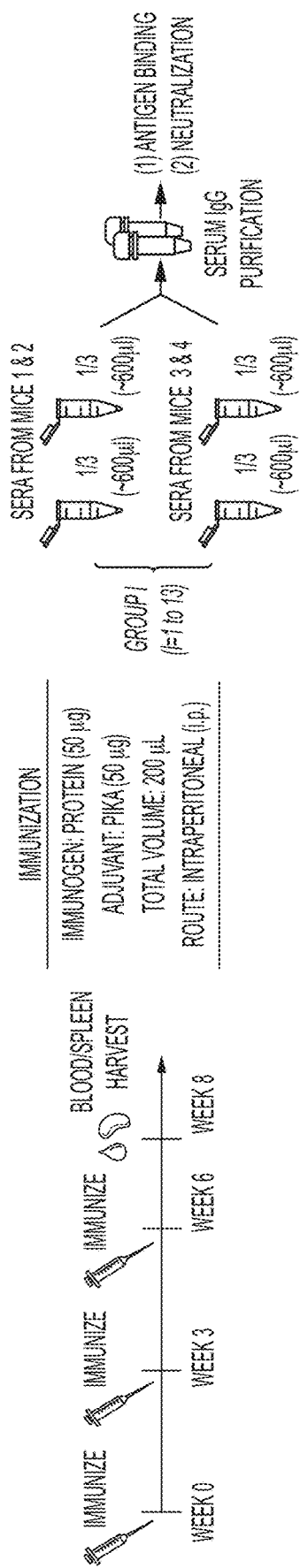
FIG. 3 shows early neutralizing antibody responses to trimers and nanoparticles in mouse immunization. (A) Schematic view of mouse immunization protocol is shown on the left, with the key parameters of formulation and immunization listed in the middle, and serum IgG purification protocol on the right. (B) Testing BG505 trimer-based immunogens and ELISA binding of purified mouse serum IgGs to three HIV-1 antigens, including BG505 UFO trimer, a ferritin nanoparticle presenting an N332 scaffold (1GUT_A_ES-FR) or an I3-01 nanoparticle presenting another N332 scaffold (1KIG_L_ES-2-I3-01), and a clade-C V1V2-ferritin nanoparticle (V1V2-FR). $EC_{50}$ values are labeled for all ELISA plots except for instances in which the highest $OD_{450}$ value is below 0.1 or in the cases of ambiguous data fitting. (C) HIV-1 neutralization by purified mouse serum IgG, with $IC_{50}$ values shown in gray shade. Higher intensity of gray shade indicates more potent neutralization. (D) Neutralization profile of group-combined mouse serum IgG from the scaffolded trimer group (S1G5). (E) Neutralization profile of group-combined mouse serum IgG and mouse-A serum IgG from the ferritin nanoparticle group (S2G1). (F) Neutralization profile of group-combined mouse serum IgG, mouse-A and mouse-D serum IgG from the I3-01 nanoparticle group (S2G5). Two HIV-1 pseudoviruses, clade-A tier-2 BG505 and clade-B tier-1 SF162, were tested with MLV included for comparison. The structural models of scaffolded gp140 trimer, ferritin nanoparticle, and I3-01 nanoparticle are shown next to the neutralization profile of group-combined mouse serum IgG.
Figure 3:
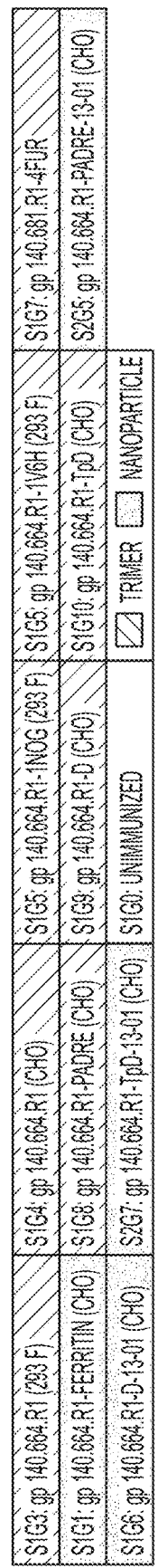
Figure 3:
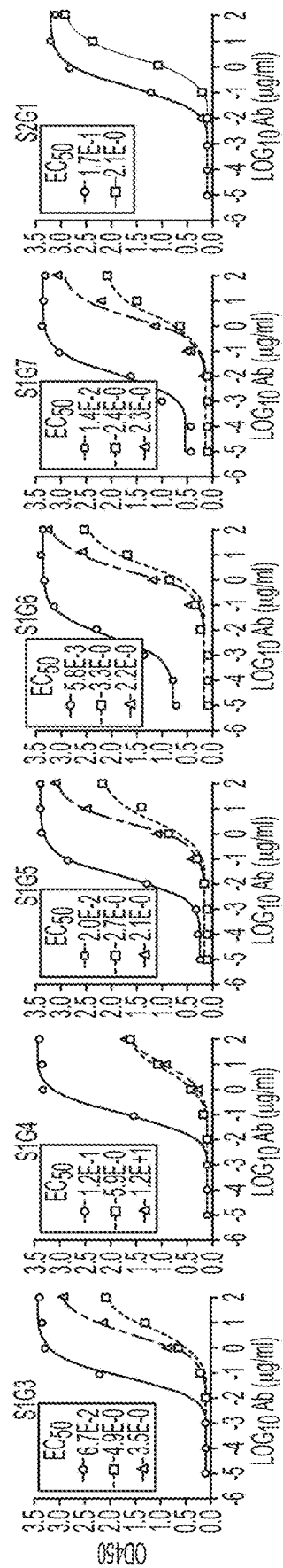
Figure 3:
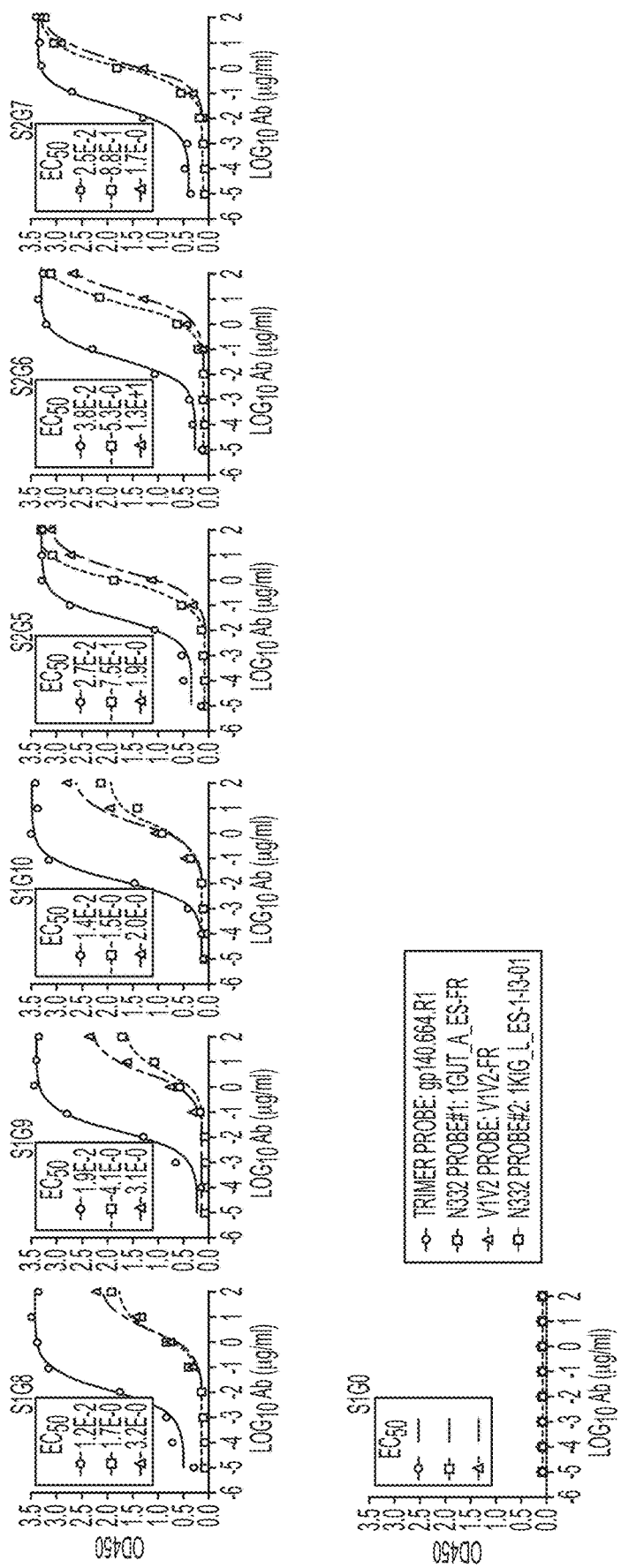
Figure 3:
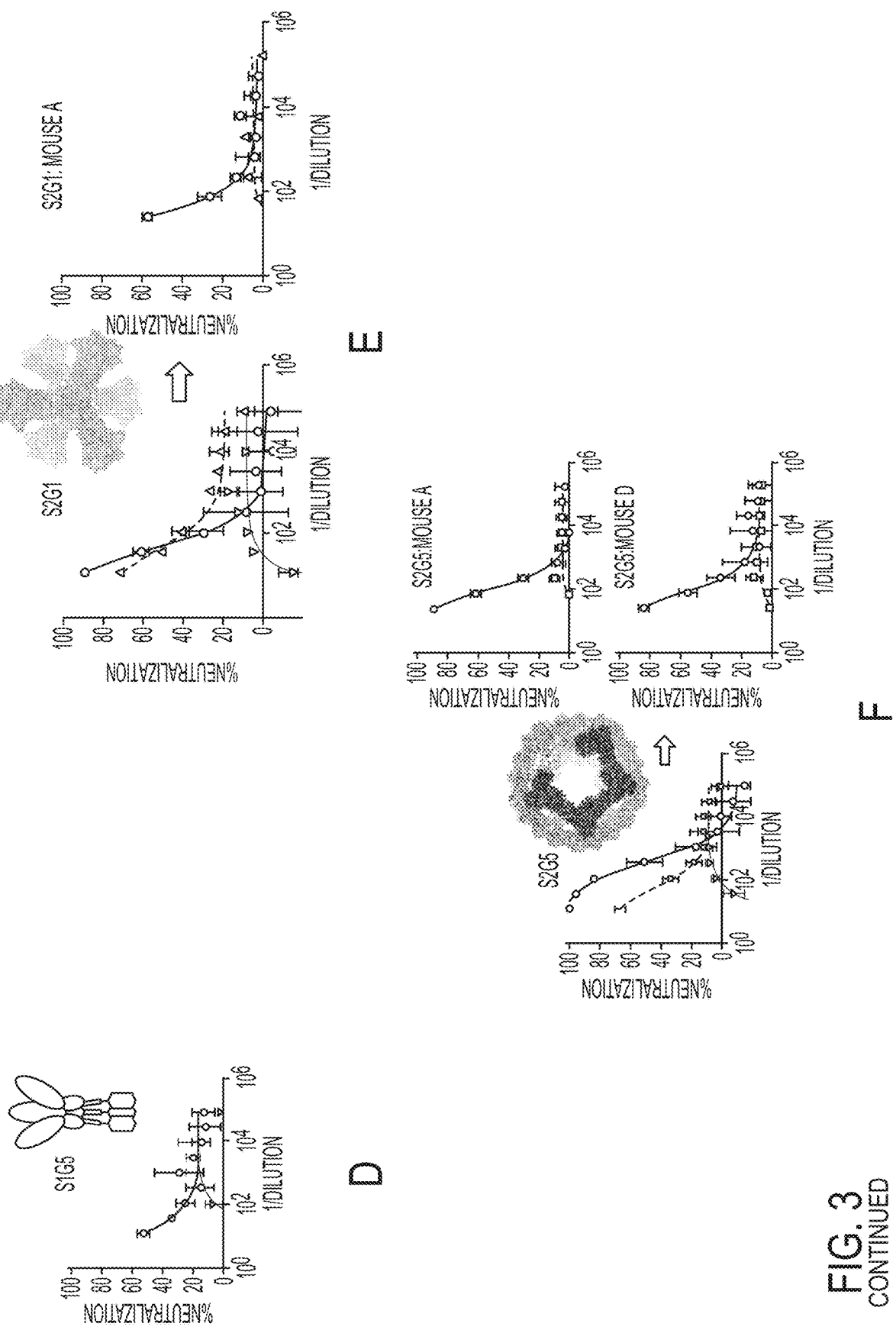

Here, we immunized the WT BALB/c mice with BG505 gp140 trimers and nanoparticles containing an HR1 redesign—the core of UFO design (Kong et al., 2016a)—using a simple six-week regimen and a serum IgG purification procedure to eliminate non-specific antiviral activity (FIG. 3A). PIKA, an human adjuvant that has shown enhanced T-cell and antibody responses in a phase-I rabies vaccine trial (Wijaya et al., 2017), was used to provide a human-compatible vaccine formulation. A total of eight trimers and four nanoparticles were tested (FIG. 3B, top), with group-combined serum IgGs assessed for antigen binding by ELISA (FIG. 3B, bottom). One V1V2 and two N332 nanoparticle probes were utilized to gauge B cell responses to the apex and the N332 supersite, respectively (Morris et al., 2017). We first examined mouse IgGs elicited by 293 F and ExpiCHO-produced trimers (S1G3 and S1G4), which exhibited differential binding to the 293 F-produced probes, confirming the cell line-specific patterns of glycosylation and B cell response (FIGS. 1D and 1E). Consistent with our previous report (Morris et al., 2017), three scaffolded gp140.681 trimers elicited strong IgG responses in mice, as indicated by the lower EC50 values (S1G5, S1G6, and S1G7). The ferritin nanoparticle (S2G1) appeared to elicit a stronger antibody response to the N332 supersite, suggesting a positive effect of multivalent display. All three gp140-T-epitope-I3-01 nanoparticles (S2G5, S2G6, and S2G7) outperformed their respective trimers containing PADRE, D, and TpD epitopes at the C terminus (S1G8, S1G9, and SIG10). Lastly, serum IgGs from twelve immunized groups were tested for HIV-1 neutralization at an IgG concentration of 3-8 mg/ml in the initial screening, with a naïve group included as control (SIG10) (FIG. 3C). In contrast with the previous negative report (Hu et al., supra), neutralization of autologous tier-2 BG505.N332 was observed for a scaffolded gp140.681 trimer (S1G5), a ferritin nanoparticle (S2G1), and two I3-01 nanoparticles (S2G5 and S2G6). When tested at a lower IgG concentration (1 mg/ml), SIG5 showed a borderline neutralization just below the threshold (FIG. 3D), whereas one subject in S2G1 (FIG. 3E) and two subjects in S2G5 appeared to have developed NAbs to the autologous tier-2 BG505.N332 (FIG. 3F). In particular, the gp140-PADRE-I3-01 nanoparticle not only exhibited outstanding purity, structural homogeneity, and antigenicity (FIG. 1, E-I), but also yielded an IC50 value indicative of rapid development of tier-2 NAbs after merely eight weeks. These data suggest that immunization with the gp140-PADRE-I3-01 nanoparticle could induce a more potent tier-2 NAb response than current trimer vaccines, likely also with improved breadth, in rabbits, NHPs, and humans.

Example 5 Other Hyperstable Nanoparticles for Presenting HIV-1 gp140 Trimer

In addition to the I3-01 nanoparticle, we also examined other stable nanoparticles for constructing the gp140-T helper epitope-nanoparticle platform HIV-1 vaccine immunogens described herein. Specifically, we tested a protein "2-Dehydro-3-Deoxyphosphogluconate Aldolase4-Hydroxy-2-Oxoglutarate Aldolase (Tm0066) From *Thermotoga maritima*" with a 2.30 Å-resolution crystal structure (PDB ID: 1VLW). The 1VLW-encoding gene sequence was used as a basis, with the 2.30 Å-resolution crystal structure used as the backbone, to design proteins that may automatically assemble into 60-meric nanoparticles with more desirable properties than I3-01. Eleven amino acids within the 1VLW sequence (SEQ ID NO:5) were subjected to the ensemble-based protein design, or visual inspection followed by manual design. Twelve designed 1VLW mutants were synthesized (SEQ ID NOs:6-17). Construction of gp140 trimer displayed on nanoparticles of these sequences, expression of the nanoparticle immunogens, and their immunogenicity are examined via the same protocols as that described above for the gp140-PADRE-I3-01 nanoparticle immunogen.

1VLW wildtype amino acid sequence (SEQ ID NO:5) (residues subject to redesign are underscored):

MKMEELFKKHKIVAVLRANSVEEAKEKALAVFEGGVHLTETTFTVPD

ADTVIKELSFLKEKGAIIGAGTVTSVEQCRKAVESGAEFIVSPHLDE

EISQFCKEKGVFYMPGVMTPTELVKAMKLGHTILKLFPGEVVGPQFV

KAMKGPFPNVKFVPTGGVNLDNVCEWFKAGVLAVGVGSALVKGTPDE

VREKAKAFVEKIRGCTE

Redesigned 1VLW variants for displaying gp140 trimer (SEQ ID NOs:6-17) (modified residues are double underlined):

>1VLW-SS1
(SEQ ID NO: 6)
MKMEELFKKHKIVAVLRANSVEEAKKKALAVFIGVHLIEITFTVPD

ADTVIKELSFLKE MGAIIGAGTVTSVEQCRKAVESGAEFIVSPHLDE

EISQFCKEKGVFYMPGVMTPTELVKAMKLGHTILKLFPGEVVGPQFV

KAMKGPFPNVKFVPTGGVNLDNVCEWFKAGVLAVGVGSALVKGTPCE

VACKAKAFVEKIRGCTE

>1VLW-MUT
(SEQ ID NO: 7)
MKMEELFKKHKIVAVLRANSVEEAKWKALAVFIGVHLIEITFTVPD

ADTVIKELSFLKELGAIIGAGTVTSVEQCRKAVESGAEFIVSPHLDE

EISQFCKEKGVFYMPGVMTPTELVKAMKLGHTILKLFPGEVVGPQFV

KAMKGPFPNVKFVPTGGVNLDNVCEWFKAGVLAVGVGSALVKGTPAE

VVEKAKAFVEKIRGCTE

>1VLW-JZ1
(SEQ ID NO: 8)
MKMEELFKKHKIVAVLRANSVEEAKMKALHVFSGGVHLIEITFTVPD

ADTVIKELSFLKEQGAIIGAGTVTSVEQCRKAVESGAEFIVSPHLDE

EISQFCKEKGVFYMPGVMTPTELVKAMKLGHTILKLFPGEVVGPQFV

KAMKGPFPNVKFVPTGGVNLDNVCEWFKAGVLAVGVGSALVKGTWDE

VSRKAKAFVEKIRGCTE

>1VLW-JZ2
(SEQ ID NO: 9)
MKMEELFKKHKIVAVLRANSVEEAKWKALHVFTGGVHLIEITFTVPD

ADTVIKELSFLKEQGAIIGAGTVTSVEQCRKAVESGAEFIVSPHLDE

EISQFCKEKGVFYMPGVMTPTELVKAMKLGHTILKLFPGEVVGPQFV

KAMKGPFPNVKFVPTGGVNLDNVCEWFKAGVLAVGVGSALVKGTWBE

VAAKAKAFVEKIRGCTE

>1VLW-JZ3
(SEQ ID NO: 10)
MKMEELFKKHKIVAVLRANSVEEAKMKALHVFTGGVHLIEITFTVPD

ADTVIKELSFLKEWGAIIGAGTVTSVEQCRKAVESGAEFIVSPHLDE

EISQFCKEKGVFYMPGVMTPTELVKAMKLGHTILKLFPGEVVGPQFV

KAMKGPFPNVKFVPTGGVNLDNVCEWFKAGVLAVGVGSALVKGTWDE

VAAKAKAFVEKIRGCTE

>1VLW-JZ4
(SEQ ID NO: 11)
MKMEELFKKHKIVAVLRANSVEEAKKKALAVFLAGVHLIEITFTVPD

ADTVIKELSFLKEMGAIIGAGTVTSVEQCRKAVESGAEFIVSPHLDE

EISQFCKEKGVFYMPGVMTPTELVKAMKLGHTILKLFPGEVVGPQFV

KAMKGPFPNVKFVPTGGVNLDNVCEWFKAGVLAVGVGSALVKGTVVE

VAAKAAFVEKIRGCTE

>1VLW-JZ5
(SEQ ID NO: 12)
MKMEELFKKHKIVAVLRANSVEEAKKKALAVFLGGVHLIEITFTVPD

ADTVIKELSFLKEMGAIIGAGTVTSVEQCRKAVESGAEFIVSPHLDE

EISQFCKEKGVFYMPGVMTPTELVKAMKLGHTILKLFPGEVVGPQFV

KAMKGPFPNVKFVPTGGVNLDNVCEWFKAGVLAVGVGSALVKGTIVE

VAAKAAFVEKIRGCTE

```
>1VLW-JZ6
                                               (SEQ ID NO: 13)
MKMEELFKKHKIVAVLRANSVEEAKKALAVFLGGVHLIEITFTVPD

ADTVIKELSFLKEMGAIIGAGTVTSVEQCRKAVESGAEFIVSPHLDE

EISQFCKEKGVFYMPGVMTPTELVKAMKLGHTILKLFPGEVVGPQFV

KAMKGPFPNVKFVPTGGVNLDNVCEWFKAGVLAVGVGSALVKGTWVE

VAAKAAAFVEKIRGCTE

>1VLW-JZ7
                                               (SEQ ID NO: 14)
MKMEELFKKHKIVAVLRANSVEEAKMKAIQVFYGGVHLIEITFTVPD

ADTVIKELSFLKEAGAIIGAGTVTSVEQCRKAVESGAEFIVSPHLDE

EISQFCKEKGVFYMPGVMTPTELVKAMKLGHTILKLFPGEVVGPQFV

KAMKGPFPNVKFVPTGGVNLDNVCEWFKAGVLAVGVGSALVKGTLAE

VAAKAIAFVEKIRGCTE

>1VLW-JZ8
                                               (SEQ ID NO: 15)
MKMEELFKKHKIVAVLRANSVEEAKMKAIHVFYGGVHLIEITFTVPD

ADTVIKELSFLKEAGAIIGAGTVTSVEQCRKAVESGAEFIVSPHLDE

EISQFCKEKGVFYMPGVMTPTELVKAMKLGHTILKLFPGEVVGPQFV

KAMKGPFPNVKFVPTGGVNLDNVCEWFKAGVLAVGVGSALVKGTWAE

VAAKAKAFVEKIRGCTE

>1VLW-JZ9
                                               (SEQ ID NO: 16)
MKMEELFKKHKIVAVLRANSVEEAKMKALAVFVGGVHLIEITFTVPD

ADTVIKELSFLKELGAIIGAGTVTSVEQCRKAVESGAEFIVSPHLDE

EISQFCKEKGVFYMPGVMTPTELVKAMKLGHTILKLFPGEVVGPQFV

KAMKGPFPNVKFVPTGGVNLDNVCEWFKAGVLAVGVGSALVKGTIAE

VAAKAAAFVEKIRGCTE

>1VLW-JZ10
                                               (SEQ ID NO: 17)
MKMEELFKKHKIVAVLRANSVEEAKMKALAVFYGGVHLIEITFTVPD

ADTVIKELSFLKEAGAIIGAGTVTSVEQCRKAVESGAEFIVSPHLDE

EISQFCKEKGVFYMPGVMTPTELVKAMKLGHTILKLFPGEVVGPQFV

KAMKGPFPNVKFVPTGGVNLDNVCEWFKAGVLAVGVGSALVKGTFVE

VAAKAAAFVEKIRGCTE
```

Example 6 Some Exemplified Experimental Procedures

Antibodies: We utilized a panel of bNAbs and non-NAbs to characterize the antigenicity of various native-like trimers and gp140 nanoparticles. Antibodies were requested from the NIH AIDS Reagent Program except for bNAbs PGDM1400, PGT145, PGT121 and PGT151, and non-NAb 19b, which were obtained internally in the Scripps Research Institute.

Expression and purification of HIV-1 Env trimers and nanoparticles: Trimers were transiently expressed in HEK293 F or ExpiCHO cells (Thermo Fisher) except for materials used for crystallographic analysis. The protocol used for trimer production in HEK293 F cells has been described previously (Kong et al., supra; Morris et al., mBio 8, e00036-00017, 2017). For cleaved HR1-redesigned trimers, the furin plasmid was added during transfection. The protocol used for trimer and nanoparticle production in ExpiCHO cells is described as follows. Briefly, ExpiCHO cells were thawed and incubated with ExpiCHO™ Expression Medium (Thermo Fisher) in a shaker incubator at 37° C., with 135 rpm and 8% $CO_2$. When the cells reached a density of $10 \times 10^6$ ml$^{-1}$, ExpiCHO™ Expression Medium was added to reduce cell density to $6 \times 10^6$ ml$^{-1}$ for transfection. The ExpiFectaminem CHO/plasmid DNA complexes were prepared for 200 ml transfection in ExpiCHO cells following the manufacturer's instruction. For SOSIP and HR1-redesigned trimers as well as the I3-01 nanoparticles presenting a BG505 HR1-redesigned trimer, 160 µg of antigen plasmid, 60 µg of furin plasmid, and 640 µl of ExpiFectamine™ CHO reagent were mixed in 15.4 ml of cold OptiPRO™ medium (Thermo Fisher), whereas for UFO and UFO$^2$ trimers as well as UFO$^2$-BG-FR nanoparticles, 200 µg of antigen plasmid was used without furin. After the first feed on day 1, ExpiCHO cells were cultured in a shaker incubator at 32° C., with 120 rpm and 8% $CO_2$ following the Max Titer protocol with an additional feed on day 5 (Thermo Fisher). Culture supernatants were harvested 13 to 14 days after transfection, clarified by centrifugation at 4000 rpm for 20 min, and filtered using a 0.45 m filter (Thermo Fisher). For timers, Env protein was extracted from the supernatants using a *Galanthus nivalis* lectin (GNL) column (Vector Labs), whereas for nanoparticles, Env-fusion protein was purified using a 2G12 affinity column. Trimers might be further purified by size exclusion chromatography (SEC) on a Superdex 200 Increase 10/300 GL column or a HiLoad 16/600 Superdex 200 PG column (GE Healthcare). The purity of I3-03 nanoparticles was characterized by SEC on a Superose 6 10/300 GL column. For both trimers and nanoparticles, protein concentration was determined using $UV_{280}$ absorbance with theoretical extinction coefficients.

Analysis of total and site-specific glycosylation profiles: The total glycan profiles of ExpiCHO and 293 F-produced trimers were generated by HILIC-UPLC. N-linked glycans were enzymatically released from envelope glycoproteins via in-gel digestion with Peptide-N-Glycosidase F (PNGase F), subsequently fluorescently labelled with 2-aminobenzoic acid (2-AA) and analyzed by HILIC-UPLC. Digestion of released glycans with Endo H enabled the quantitation of oligomannose-type glycans. The compositions of the glycans were determined by analyzing released glycans from trimers by PNGase F digestion using ion mobility MS. Negative ion mass, collision-induced dissociation (CID) and ion mobility spectra were recorded with a Waters Synapt G2Si mass spectrometer (Waters Corp.) fitted with a nano-electrospray ion source. Waters Driftscope (version 2.8) software and MassLynx™ (version 4.1) was used for data acquisition and processing. Spectra were interpreted as described previously (Harvey et al., Anal. Biochem. 376, 44-60, 2008). The results obtained served as the basis for the creation of sample-specific glycan libraries, which were used for subsequent site-specific N-glycosylation analyses. For site-specific N-glycosylation analysis, before digestion, trimers were denatured and alkylated by incubation for 1 h at room temperature (RT) in a 50 mM Tris/HCl, pH 8.0 buffer containing 6 M urea and 5 mM dithiothreitol (DTT), followed by the addition of 20 mM iodacetamide (IAA) for a further 1 h at RT in the dark, and then additional DTT (20 mM) for another 1 h, to eliminate any residual IAA. The alkylated trimers were buffer-exchanged into 50 mM Tris/HCl, pH 8.0 using Vivaspin columns and digested separately with trypsin and chymotrypsin (Mass Spectrometry Grade, Promega) at a ratio of 1:30 (w/w). Glycopeptides were selected from the protease-digested samples using the ProteoExtract Glycopeptide Enrichment Kit (Merck Millipore). Enriched glycopeptides were analyzed by LC-ESI MS on an Orbitrap fusion mass spectrometer (Thermo Fisher Scientific), using higher energy collisional dissociation (HCD) fragmentation. Data analysis and glycopeptide identification were performed using Byonic™ (Version 2.7) and Byologic™ software (Version 2.3; Protein Metrics Inc.).

BN-PAGE: Env proteins and nanoparticles were analyzed by blue native polyacrylamide gel electrophoresis (BN-PAGE) and stained with Coomassie blue. The protein samples were mixed with G250 loading dye and added to a 4-12% Bis-Tris NuPAGE gel (Life Technologies). BN-PAGE gels were run for 2.5 hours at 150 V using the NativePAGE™ running buffer (Life Technologies) according to the manufacturer's instructions.

Differential scanning calorimetry (DSC): Thermal stability of UFO²-BG trimers, UFO²-U trimers, and trimer-presenting nanoparticles was measured using a MicroCal VP-Capillary calorimeter (Malvern) in PBS buffer at a scanning rate of $90°$ $C.h^{-1}$ from $20°$ C. to $120°$ C. Data were analyzed using the VP-Capillary DSC automated data analysis software.

Protein production and purification for crystallization: The clade-B tier-3 H078.14 UFO²-BG trimer was expressed in FreeStyle 293 S cells and purified from culture supernatant using a 2G12-coupled affinity matrix followed by size exclusion chromatography (SEC). Fabs PGT124 and 35022 were transiently transfected into mammalian FreeStyle 293F cells (Invitrogen) and purified using a LC-X capture select column, prior to further purification by ion exchange chromatography and SEC on a Superdex 200 16/60 column. The trimer complexes were prepared by mixing H078.14 $UFO^2$-BG trimer protein with PGT124 and 35022 at a molar ratio of 1:3:2 for 30 min at room temperature. To decrease heterogeneity on trimer complexes, deglycosylation was carried out on H078.14 $UFO^2$-BG.664 produced in 293S cells with Endoglycosidase H (New England Biolabs) overnight at 4° C. The trimer complexes were subjected to crystal trials after further purification of the complexes by SEC.

Protein crystallization and data collection: The SEC-purified H078.14 $UFO^2$-BG trimer complexes was concentrated to ~5 mg/ml before subjected to extensive crystallization trials at both 4° C. and 20° C. Crystals for protein complex containing Fab PGT124 and 35022 bound to $UFO^2$-BG trimer were obtained from 0.1 M calcium acetate, 0.1 M MES (pH 6.0), 15% (v/v) PEG400, and harvested and cryo-protected with 25% glycerol, followed by immediate flash cooling in liquid nitrogen. In current condition, the best crystal was diffracted to 6.20 Å resolution and the data was collected at beamline 12-2 at the Stanford Synchtron Radiation Lightsource, processed with HKL-2000, and indexed in space group $P6_3$ with 99.7% completeness with unit cell parameters a=b=129.3 Å, c=314.5 Å.

Structure determination and refinement: The H078.14 $UFO^2$-BGtrimer structure bound to PGT124 and 35022 were solved by molecular replacement (MR) using Phaser with the one protomer of 35022:BG505 SOSIP.664 structure (PDB: 5CEZ), and PGT124 Fab structure (PDB: 4R26). The structures were refined using Phenix, with Coot used for model building and MolProbity for structure validation. Due to the limited resolution of the datasets, two B-factor groups per residue refinement were used. Furthermore, positional coordinate refinement was enforced using a reference model set of restraints. The final $R_{cryst}$ and $R_{free}$ values for complex structure are 25.0% and 31.4%. Figures were generated with PyMol and Chimera. In the crystal structure, the residues were numbered according to the Kabat definition for FAbs and according to the HXBc2 system for gp140.

Negative-stain electron microscopy: $UFO^2$-BG trimers and trimer-presenting nanoparticles were analyzed by negative-stain EM. A 3 μL aliquot containing ~0.01 mg $ml^{-1}$ of the trimers or nanoparticles was applied for 15 s onto a carbon-coated 400 Cu mesh grid that had been glow discharged at 20 mA for 30 s, then negatively stained with 2% (w/v) uranyl formate for 30 s. Data were collected using a FEI Tecnai Spirit electron microscope operating at 120 kV, with an electron dose of ~25 $e^- Å^{-2}$ and a magnification of 52,000× that resulted in a pixel size of 2.05 Å at the specimen plane. Images were acquired with a Tietz 4k×4k TemCan-F416 CMOS camera using a nominal defocus of 1500 nm and the Leginon package. $UFO^2$-BG trimer particles were selected automatically from the raw micrographs using DoG Picker, while trimer-presenting nanoparticles were selected manually using the Appion Manual Picker. Both were put into particle stack using the Appion software package. Reference-free, two-dimensional (2D) class averages were calculated using particles binned by two via iterative multivariate statistical analysis (MSA)/multireference alignment (MRA) and sorted into classes. To analyze the quality of the trimers (native-like and non-native), the reference free 2D class averages were examined by eye as previously described (de Taeye et al., Cell 163, 1702-1715, 2015).

Bio-Layer Interferometry (BLI): The kinetics of trimer and nanoparticle binding to bNAbs and non-NAbs was measured using an Octet Red96 instrument (forteBio, Pall Life Sciences). All assays were performed with agitation set to 1000 rpm in forteBio 1× kinetic buffer. The final volume for all the solutions was 200 μl per well. Assays were performed at 30° C. in solid black 96-well plates (Geiger Bio-One). 5 μg $ml^{-1}$ of antibody in 1× kinetic buffer was loaded onto the surface of anti-human Fc Capture Biosensors (AHC) for 300 s. A 60 s biosensor baseline step was applied prior to the analysis of the association of the antibody on the biosensor to the antigen in solution for 200 s. A two-fold concentration gradient of antigen, starting at 200 nM for trimers and 14-35 nM for nanoparticles depending on the size, was used in a titration series of six. The dissociation of the interaction was followed for 300 s. Correction of baseline drift was performed by subtracting the mean value of shifts recorded for a sensor loaded with antibody but not incubated with antigen and for a sensor without antibody but incubated with antigen. Octet data were processed by forteBio's data acquisition software v.8.1. Of note, for apex-directed bNAbs, experimental data were fitted with the binding equations describing a 2:1 interaction to achieve the optimal fitting results.

B cell activation assay: Generation of K46 B-cell lines expressing PGT121, PGT145 or VRCO1 has been previously described (Ota et al., J. Immunol. 189, 4816-48242012). In brief, K46 cells expressing a doxycyclin-inducible form of bNAb B cell receptors (BCRs) were maintained in advanced DMEM (Gibco), supplemented with 10% FCS, Pen/Strep antibiotics, and 2 μg $ml^{-1}$ Puromycin (Gibco). Cells were treated overnight in 1 μg $ml^{-1}$ doxycyclin (Clontech) to induce human BCR expression. After loading with Indo-1 (Molecular Probes) at 1 μM for one hour at 37° C., washed cells were stimulated with the indicated agents at a concentration of 10 μg $ml^{-1}$: anti-mouse IgM (Jackson ImmunoResearch); $UFO^2$-BG or an HR1-redesigned gp140 trimer with a T-helper epitope (PADRE) fused to the C-terminus; UFO²-BG-FR or I3-01 nanoparticle presenting an HR1-redesigned gp140 trimer. Calcium mobilization was assessed on a LSR II flow cytometer (BD). In each run, the unstimulated B cells were first recorded for 60 s, with the testing immunogen added, mixed thoroughly, and recorded for 180 s, followed by addition of 1 μl of 1 μg ml⁻¹ ionomycin (Sigma) and recording for another 60 s to verify indo loading.

Mouse immunization and serum IgG purification: Seven-week-old BALB/c mice were purchased from The Jackson Laboratory. The nice were housed in ventilated cages in environmentally controlled rooms at TSRI, in compliance with an approved IACUC protocol and AAALAC guidelines. At week 0, each mouse was immunized with 200 μl of antigen/adjuvant mix containing 50 μg of antigen and 100 μl AddaVax adjuvant (Invivogen) or 50 μl PIKA adjuvant (Yisheng Biopharma) per manufacturer's instruction via the intraperitoneal (i.p.) route. At week 3 and week 6, the animals were boosted with 50 μg of antigen formulated in AddaVax or PIKA adjuvant. At week 8, the animals were terminally bled through the retro orbital membrane using heparinized capillary tubes. Samples were diluted with an equal volume of PBS and then overlayed on 4.5 ml of Ficoll/Histopaque in a 15 ml SepMate tube (StemCell) and spun at 1200 RPM for 10 min at 20° C. to separate plasma and cells. The plasma was heat inactivated at 56° C. for 1 hour, spun at 1200 RPM for 10 min and sterile filtered. The cells were washed once in PBS and then resuspended in 1 ml of ACK Red Blood Cell lysis buffer (Lonza). After 2 rounds of washing with PBS, PBMCs were resuspended in 2 ml of Bambanker Freezing Media (Lymphotec Inc.). Spleens were also harvested and grounded against a 40-μm cell strainer (BD Falcon) to release the splenocytes into a cell suspension. The cells were centrifuged, washed in PBS and then treated with 10 ml of RBC lysis buffer as per manufacturer specifications, and resuspended in Bambanker Freezing Media for cell freezing. One-third of the total serum per mouse, or 600 μl of serum, was purified using a 0.2-ml protein G spin kit (Thermo Scientific) following the manufacturer's instructions. Purified serum IgGs obtained from four mice within each group were combined for characterization by ELISA and HIV-1 neutralization assays.

Enzyme-linked immunosorbent assay (ELISA): Each well of a Costar™ 96-well assay plate (Corning) was first coated with 50 μl PBS containing 0.2 μg of the appropriate antigens. The plates were incubated overnight at 4° C., and then washed five times with wash buffer containing PBS and 0.05% (v/v) Tween 20. Each well was then coated with 150 μl of a blocking buffer consisting of PBS, 20 mg ml⁻¹ blotting-grade blocker (Bio-Rad), and 5% (v/v) FBS. The plates were incubated with the blocking buffer for 1 hour at room temperature, and then washed 5 times with wash buffer. Purified mouse IgGs were diluted in the blocking buffer to a maximum concentration of 100 μg ml⁻¹, followed by a 10-fold dilution series. For each antibody dilution, a total of 50 μl volume was added to the appropriate wells. Each plate was incubated for 1 h at room temperature, and then washed 5 times with wash buffer. A 1:2000 dilution of horseradish peroxidase (HRP)-labeled goat anti-mouse IgG antibody (Jackson ImmunoResearch Laboratories) was then made in the wash buffer, with 50 μl of this diluted secondary antibody added to each well. The plates were incubated with the secondary antibody for 1 hr at room temperature, and then washed 5 times with wash buffer. Finally, the wells were developed with 50 μl of TMB (Life Sciences) for 3-5 min before stopping the reaction with 50 μl of 2 N sulfuric acid. The resulting plate readouts were measured at a wavelength of 450 nm.

Pseudovirus production and neutralization assays: Pseudoviruses were generated by transfection of 293 T cells with an HIV-1 Env expressing plasmid and an Env-deficient genomic backbone plasmid (pSG3ΔEnv), as described previously. Pseudoviruses were harvested 72 hours post-transfection for use in neutralization assays. Neutralizing activity of purified mouse serum IgGs was assessed using a single round of replication pseudovirus assay and TZM-bl target cells, as described previously. Briefly, TZM-bl cells were seeded in a 96-well flat bottom plate. To this plate was added pseudovirus, which was preincubated with serial dilutions of mouse serum IgG for 1 hour at 37° C. Luciferase reporter gene expression was quantified 72 hours after infection upon lysis and addition of Bright-Glo™ Luciferase substrate (Promega). To determine IC50 values, dose-response curves were fit by nonlinear regression.

Mouse repertoire sequencing and bioinformatics analysis: A 5'-RACE protocol has been developed for unbiased sequencing of mouse B-cell repertoires, as previously described. Briefly, RNA (including mRNA) was extracted from total PBMCs of each mouse into 30 μl of water with RNeasy Mini Kit (Qiagen). 5'-RACE was performed with SMARTer RACE cDNA Amplification Kit (ClonTech). The immunoglobulin PCRs were set up with Platinum Taq High-Fidelity DNA Polymerase (Life Technologies) in a total volume of 50 μl, with 5 μl of cDNA as template, 1 μl of 5'-RACE primer, and 1 μl of 10 μM reverse primer. The 5'-RACE primer contained a PGM/S5 P1 adaptor, while the reverse primer contained a PGM/S5 A adaptor. We adapted the mouse 3'-$C_\gamma$1-3 and 3'-$C_\mu$ inner primers as reverse primers for 5'-RACE PCR processing of the heavy chains. A total of 25 cycles of PCR was performed and the expected PCR products (500-600 bp) were gel purified (Qiagen). NGS was performed on the Ion S5 system. Briefly, heavy chain libraries from the same group were quantitated using Qubit® 2.0 Fluorometer with Qubit® dsDNA HS Assay Kit, and then mixed using a ratio of 1:1:1:1 for sequencing. Template preparation and (Ion 520) chip loading were performed on Ion Chef using the Ion 520/530 Ext Kit, followed by sequencing on the Ion S5 system with default settings. The mouse antibodyomics pipeline was used to process the raw data and to determine the distributions of heavy chain germline gene usage.

Example 7 T-Helper Epitope-Encapsulated Nanoparticles

Figure 4:
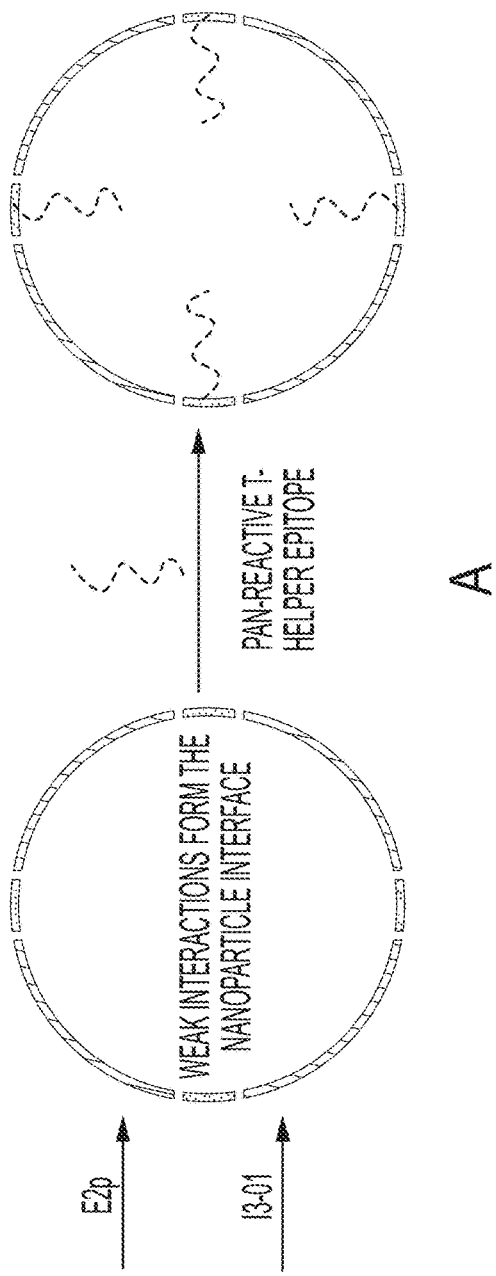
FIG. 4 shows the design concept, SEC profile, and negative-stain EM image of HIV-1 gp140 trimer-presenting nanoparticle with a T-helper epitope fused to the C-terminus of the nanoparticle subunit. (A) Schematic drawing of E2p and I3-01 nanoparticle design with a pan-reactive T-helper epitope fused to the C-terminus of the nanoparticle subunit. (B) SEC profiles of BG505 gp140 trimer-presenting E2p and I3-01 nanoparticles obtained from a Superose 6 10/300 GL column after purification using a 2G12 antibody affinity column. (C) Raw micrographs of BG505 gp140 trimer-presenting E2p and I3-01 nanoparticles obtained from negative-stain EM.
Figure 4:
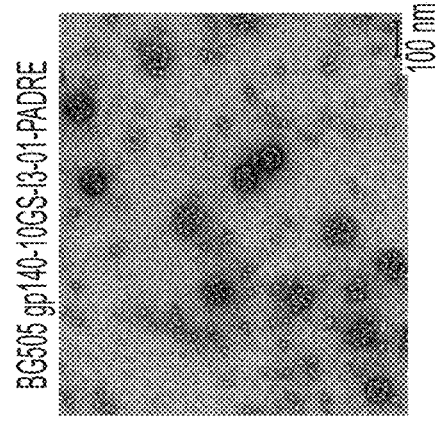
Figure 4:
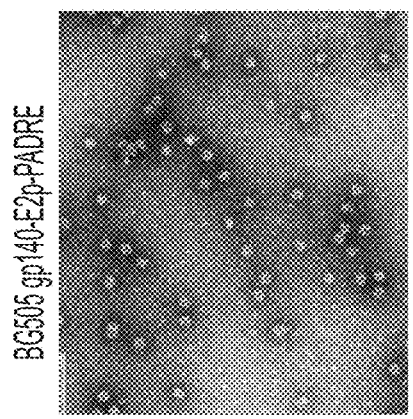
Figure 4:
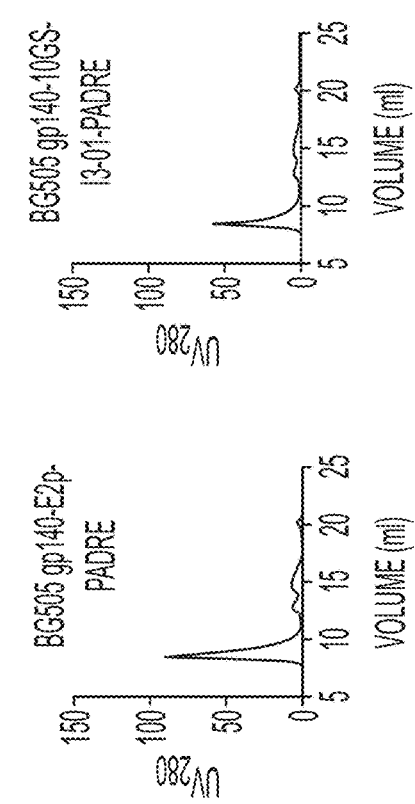

Although the use of a T-helper epitope as a linker to connect HIV-1 gp140 and nanoparticle backbone produced HIV-1 trimer-presenting nanoparticles with desirable antigenic and immunogenic properties (FIGS. 1-3), the assembly of such nanoparticles appeared to be affected by the hydrophobic T-helper epitopes exposed on the nanoparticle surface. To improve nanoparticle assembly and purity, an alternative strategy for incorporating T-cell helper epitope into nanoparticle vaccine design was examined. Instead of inserting a T-helper epitope between antigen and nanoparticle backbone on the outside surface, this T-helper epitope was genetically fused to the C-terminus of the nanoparticle subunit via a short, flexible peptide spacer. The expected outcome would be a nanoparticle vaccine with twenty HIV-1 gp140 trimers displayed on the outside surface and sixty hydrophobic T-helper epitopes encapsulated inside the nanoparticle shell (FIG. 4A). This design was devised based on the observations that both E2p and I3-01 are large 60-meric nanocages with hollow interiors and that almost all proteins prefer a hydrophobic core and a charged/hydrophilic surface to achieve stability in solution.

We tested this strategy with a pan-reactive T-helper epitope, PADRE. In the construct design, the C-terminus of HIV-1 BG505 gp140 was fused to the N-terminus of the nanoparticle subunit with a 1G spacer (for E2p) or with a 10aa GGGGSGGGGS (SEQ ID NO:20) spacer (for I3-01), both of which contained an enzymatic site (AS) preceding the spacer, and then the N-terminus of PADRE was fused to the C-terminus of the nanoparticle subunit with a 5aa GGGGS (SEQ ID NO:4) spacer. The two resulting fusion constructs were expressed transiently in 25 ml of ExpiCHO cells and purified using a 2G12 antibody affinity column. The obtained protein was analyzed by size-exclusion chromatography (SEC) on a Superose 6 10/300 GL column. For both constructs, we observed peaks at 6-7 mL corresponding to well-formed nanoparticles (FIG. 4B). Considering the smaller-scale transfection (25 ml vs 100 ml in FIG. 1F), the actual nanoparticle yield was notably improved compared to the design in which the T-helper epitope is used as a linker outside the nanoparticle. The 2G12-purified nanoparticles were further analyzed by negative-stain EM. Fully assembled nanoparticles with spikes on the surface can be recognized from the raw micrographs derived from negative-stain EM (FIG. 4C). Taken together, SEC and EM data confirmed that T-helper epitope encapsulation might presents an effective strategy for designing HIV-1 nanoparticle vaccines with embedded T-cell help.

A T-helper epitope can be fused to the C-terminus of the subunit of a self-assembling nanoparticle via a short peptide spacer. The C-terminus of HIV-1 gp140 can be fused to the N-terminus of the subunit of the abovementioned nanoparticle. When these fusion subunits assemble into a nanoparticle, it will present 8 or 24 HIV-1 gp140 trimers on the outside surface of the nanoparticle while encapsulating 24 or 60 T-helper epitopes inside the nanoparticle shell. The HIV-1 gp140 trimers on the outside surface of the nanoparticle will induce an anti-HIV-1 B-cell response, while the dense cluster of T-helper epitopes inside the nanoparticle will induce a broadly reactive T-cell response upon the digestion of the nanoparticle protein.

The invention thus has been disclosed broadly and illustrated in reference to representative embodiments described above. It is understood that various modifications can be made to the present invention without departing from the spirit and scope thereof.

It is further noted that all publications, sequence accession numbers, patents and patent applications cited herein are hereby expressly incorporated by reference in their entirety and for all purposes as if each is individually so denoted. Definitions that are contained in text incorporated by reference are excluded to the extent that they contradict definitions in this disclosure.

What is claimed is:

1. A polynucleotide sequence encoding a HIV-1 vaccine immunogen that comprises an HIV-1 Env-derived trimer protein presented on a self-assembling nanoparticle, wherein a linker sequence (a) is fused to the C-terminus of the nanoparticle subunit while the HIV-1 trimer protein subunit is fused to the N-terminus of the nanoparticle subunit or (b) links the HIV-1 trimer protein to the N-terminus of the nanoparticle subunit, wherein the self-assembling nanoparticle has a subunit sequence as shown in any one of SEQ ID NOs:6-17 or a conservatively modified variant thereof.

2. The polynucleotide sequence of claim 1, wherein the HIV-1 Env-derived trimer protein is an uncleaved prefusion-optimized (UFO) gp140 trimer.

3. The polynucleotide sequence of claim 2, wherein the UFO gp140 trimer is a chimeric trimer comprising a redesigned gp41$_{ECTO}$ domain from HIV-1 strain BG505, wherein the redesigned gp41$_{ECTO}$ domain contains (a) HR1 N-terminal bend replaced with a stabilizing loop sequence and (b) a cleavage-site linker.

4. The polynucleotide sequence of claim 1, wherein the linker sequence comprises a T-helper epitope sequence or a glycine-serine linker or both.

5. The polynucleotide sequence of claim 1, wherein the linker sequence comprises the sequence as shown in any one of SEQ ID NOs:1-3, or a conservatively modified variant thereof.

6. The polynucleotide sequence of claim 1, wherein the linker sequence comprises 1 to 5 tandem repeats of GGGGS (SEQ ID NO:4) or GSGSG (SEQ ID NO:19).

7. The polynucleotide sequence of claim 1, wherein the linker sequence is fused to the C-terminus of the nanoparticle subunit via a short peptide spacer, and a second peptide spacer links the HIV-1 trimer protein subunit to the N-terminus of the nanoparticle subunit.

8. The polynucleotide sequence of claim 1, wherein the self-assembling nanoparticle comprises a trimeric sequence.

9. The polynucleotide sequence of claim 1, wherein the HIV-1 Env-derived trimer protein is gp140.

10. The polynucleotide sequence of claim 1, wherein the HIV-1 Env-derived trimer protein is an uncleaved prefusion-optimized (UFO) gp140 trimer.

11. The polynucleotide sequence of claim 10, wherein the UFO gp140 trimer is a chimeric trimer comprising a redesigned gp41$_{ECTO}$ domain from HIV-1 strain BG505, wherein the redesigned gp41$_{ECTO}$ domain contains (a) HR1 N-terminal bend replaced with a stabilizing loop sequence and (b) a cleavage-site linker.

12. The polynucleotide sequence of claim 10, wherein the HIV-1 Env-derived trimer is an UFO gp140 trimer, the self-assembling nanoparticle is generated with a subunit sequence as shown in any one of SEQ ID NOs:6-17, and the linker sequence comprises the sequence as shown in SEQ ID NO:1.

13. The polynucleotide sequence of claim 7, wherein the linker sequence is encapsulated within the nanoparticle.

14. An expression vector that harbors the polynucleotide sequence of claim 1.

15. An isolated host cell that harbors the polynucleotide sequence of claim 1.

16. A pharmaceutical composition, comprising the polynucleotide sequence of claim 1 and a pharmaceutically acceptable carrier.

17. A method of inducing an HIV-1 neutralizing antibody in a subject, comprising administering to the subject a therapeutically effective amount of the pharmaceutical composition of claim 16, thereby inducing a HIV-1 neutralizing antibody in the subject.

18. The method of claim 17, wherein HIV-1 vaccine immunogen comprises an UFO gp140 trimer, a self-assembling nanoparticle generated with a subunit sequence as shown in any one of SEQ ID NOs:6-17, and a T-helper epitope sequence comprising the sequence as shown in SEQ ID NO:1, wherein the T-helper epitope sequence (a) is fused to the C-terminus of the nanoparticle subunit via a short peptide spacer while the UFO gp140 trimer subunit is fused to the N-terminus of the nanoparticle subunit or (b) covalently links the UFO gp140 trimer subunit at its C-terminus to the N-terminus of the nanoparticle subunit.

19. The method of claim 18, wherein the T-helper epitope sequence fused to the C-terminus of the nanoparticle subunit is encapsulated within the nanoparticle upon self-assembly of the nanoparticle.

20. The method of claim 17, wherein the HIV-1 Env-derived trimer protein is an uncleaved prefusion-optimized (UFO) gp140 trimer.

21. The method of claim 20, wherein the UFO gp140 trimer is a chimeric trimer comprising a redesigned gp41$_{ECTO}$ domain from HIV-1 strain BG505, wherein the redesigned gp41$_{ECTO}$ domain contains (1) HR1 N-terminal bend replaced with a stabilizing loop sequence and (2) a cleavage-site linker.

* * * * *